US010960048B2

(12) United States Patent
Åkerström et al.

(10) Patent No.: US 10,960,048 B2
(45) Date of Patent: Mar. 30, 2021

(54) ALPHA-1-MICROGLOBULIN FOR USE IN THE PROTECTION OF KIDNEYS IN RADIONUCLIDE THERAPY

(71) Applicant: Guard Therapeutics International AB, Lund (SE)

(72) Inventors: Bo Åkerström, Lund (SE); Sven-Erik Strand, Lund (SE); Magnus Göran Gram, Oxie (SE); Amanda Thuy Tran, Malmö (SE)

(73) Assignee: Guard Therapeutics International AB, Lund (SE)

( * ) Notice: Subject to any disclaimer, the term of this patent is extended or adjusted under 35 U.S.C. 154(b) by 0 days.

(21) Appl. No.: 15/552,478

(22) PCT Filed: Feb. 25, 2016

(86) PCT No.: PCT/EP2016/053904
§ 371 (c)(1),
(2) Date: Aug. 21, 2017

(87) PCT Pub. No.: WO2016/135214
PCT Pub. Date: Sep. 1, 2016

(65) Prior Publication Data
US 2018/0243369 A1    Aug. 30, 2018

(30) Foreign Application Priority Data

Feb. 25, 2015 (DK) .................................. 2015 70099

(51) Int. Cl.
*A61K 51/08* (2006.01)
*A61K 38/17* (2006.01)
*A61P 13/12* (2006.01)

(52) U.S. Cl.
CPC .......... *A61K 38/1722* (2013.01); *A61K 51/08* (2013.01); *A61K 51/083* (2013.01); *A61P 13/12* (2018.01); *G01N 2333/8117* (2013.01); *Y02A 50/30* (2018.01)

(58) Field of Classification Search
CPC .. A61K 398/00; A61K 38/1722; A61K 51/00; A61K 51/08; A61K 51/083; A61K 38/00; A61P 13/12; G01N 2333/8117
USPC .......... 424/1.11, 1.65, 1.69, 1.81, 1.85, 1.89, 424/9.1, 9.2; 206/223, 569, 570; 530/300, 311, 317, 350; 534/7, 10–16; 514/1, 1.1, 19.2, 19.3, 19.4, 19.5, 19.6, 514/21.1, 21.2
See application file for complete search history.

(56) References Cited

U.S. PATENT DOCUMENTS

2014/0228233 A1*  8/2014  Pawlowski .......... C12Q 1/6886
506/9

FOREIGN PATENT DOCUMENTS

| EP | 1 862 172 A1 | 12/2007 |
| WO | WO 00/37099 A2 | 6/2000 |
| WO | WO 2014/039987 A2 | 3/2014 |

OTHER PUBLICATIONS

Zaknun et al, Eur. J. Nucl. Med. Mol. Imaging (Feb. 7, 2013), vol. 40, pp. 800-816 (Year: 2013).*
Åkerström et al., "A1M, an Extravascular Tissue Cleaning and Housekeeping Protein," Free Radical Biology and Medicine (2014) vol. 74, pp. 274-282.
Åkerström et al., "The Lipocalin $\alpha_1$-Microglobulin Has Radical Scavenging Activity," The Journal of Biological Chemistry (Oct. 2007) vol. 282, No. 43, pp. 31493-31503.
Allhorn et al., "Processing of the Lipocalin $\alpha_1$-Microglobulin by Hemoglobin Induces Heme-Binding and Heme-Degradation Properties," Blood (Mar. 2002) vol. 99, No. 6, pp. 1894-1901.
Allhorn et al., "Redox Properties of the Lipocalin $\alpha_1$-Macroglobulin: Reduction of Cytochrome c, Hemoglobin, and Free Iron," Free Radical Biology & Medicine (2005) vol. 38, pp. 557-567.
Azzam et al., "Oxidative Metabolism, Gap Junctions and the Ionizing Radiation-Induced Bystander Effect," Oncogene (2003) vol. 22, pp. 7050-7057.
Bäck et al, "Glomerular Filtration Rate After Alpha-Radioimmunotherapy with $^{211}$At-MX35-F(ab')$_2$: A Long-Term Study of Renal Function in Nude Mice, Cancer Biotherapy and Radiopharmaceuticals," (2009) vol. 24, No. 6, pp. 649-658.
De Jong et al., "New Advances in Peptide Receptor Radionuclide Therapy," The Journal of Nuclear Medicine (May 2002) vol. 43, No. 5, pp. 617-620.
Greenwood et al., "The Preparation of $^{131}$I-Labelled Human Growth Hormone of High Specific Radioactivity," Biochem. J. (1963) vol. 89, pp. 114-123.
Halliwell et al., "The Definition and Measurement of Antioxidants in Biological Systems," Free Radical Biology & Medicine (1995) vol. 18, No. 1, pp. 125-126.
Krenning et al., "Localisation of Endocrine-Related Tumours with Radioiodinated Analogue of Somatostatin," The Lancet (Feb. 1989) pp. 242-244.
Kwasek et al., "Production of Recombinant Human $\alpha_1$-microglobulin and Mutant Forms Invovled in Chromophore Formation," Protein Expression and Purification (2007) vol. 53, pp. 145-152.
Laemmli et al., "Cleavage of Structural Proteins During the Assembly of the Head of Bacteriophage T4," Nature (Aug. 1970) vol. 227, pp. 680-685.
Larsson et al., "Distribution of Iodine 125-labeled $\alpha_1$-Microglobulin in Rats After Intravenous Injection," J. Lab. Clin. Med. (Mar. 2001) pp. 165-175.
Little et al. "Bystander Effects: Intercellular Transmission of Radiation Damage Signals," Radiation Protection Dosimetry (2002) vol. 99, Nos. 1-4, pp. 159-162.

(Continued)

*Primary Examiner* — D. L. Jones
(74) *Attorney, Agent, or Firm* — Dinsmore & Shohl LLP; Weston R. Gould

(57) ABSTRACT

This invention relates to $\alpha_1$-microglobulin (A1M) for use in the diagnosis or treatment of malignancies requiring radionuclide diagnostics (RD), radionuclide therapy (RNT) or radioimmunotherapy (RIT), respectively, wherein A1M is used as a co-treatment to RD, RNT or RIT.

Figure 1:
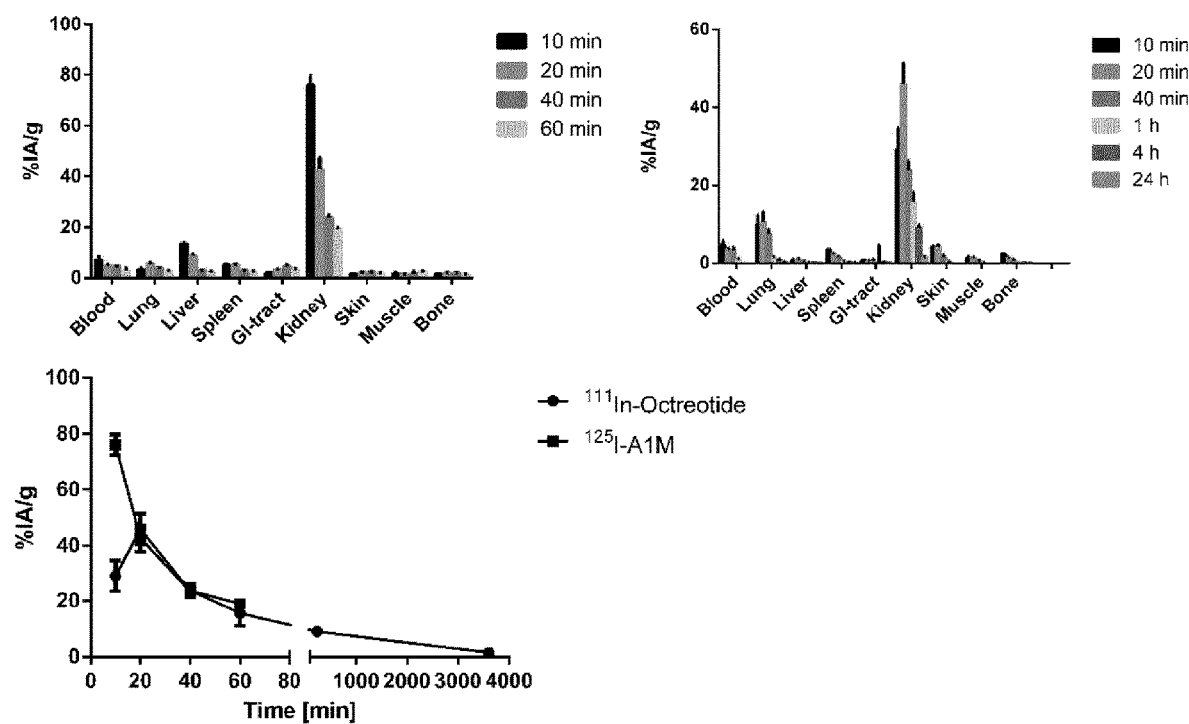

11 Claims, 16 Drawing Sheets
Specification includes a Sequence Listing.

(56) References Cited

OTHER PUBLICATIONS

Lyng et al., "Initiation of Apoptosis in Cells Exposed to Medium from the Progeny of Irradiated Cells: A Possible Mechanism for Bystander-Induced Genomic Instability?," Radiation Research (2002) vol. 157, No. 4, pp. 365-370.

Lyng et al., "Production of a Signal by Irradiated Cells which Leads to a Response in Unirradiated Cells Characteristic of Initiation of Apoptosis," British Journal of Cancer (2000) vol. 83, No. 9, pp. 1223-1230.

May et al., "Perfusion of Human Placenta with Hemoglobin Introduces Preeclampsia-Like Injuries that are Prevented by $\alpha_1$-Microglobulin," Placenta (2011) vol. 32, pp. 323-332.

Mothersill et al. "Radiation-Induced Bystander Effects: Past History and Future Directions," Radiation Research (2001) vol. 155, No. 6, pp. 759-767.

Norberg et al., "Quantitative and Qualitative Evaluation of Plasma and Urine a1-Microglobulin in Healthy Donors and Patients with Different Haemolytic Disorders and Haemochromatosis," Clinica Chimica Acta (2007) vol. 386, pp. 31-37.

Ollson et al., "The Lipocalin $\alpha_1$-Microglobulin Protects Erythroid K562 Cells Against Oxidative Damage Induced by Heme and Reactive Oxygen Species," Free Radical Research (Aug. 2008) vol. 42, No. 8, pp. 725-736.

Olsson et al., "Bystander Cell Death and Stress Response is Inhibited by the Radical Scavenger $\alpha_1$-Microglobulin in Irradiated Cell Cultures," Radiation Research 174, (2010) vol. 174, pp. 590-600.

Olsson et al., "Pathological Conditions Involving Extracellular Hemoglobin: Molecular Mechanisms, Clinical Significance, and Novel Therapeutic Opportunities for $\alpha_1$-Microglobulin," Antioxidants & Redox Signaling (2012) pp. 1-34.

Olsson et al., "The Radical-Binding Lipocalin Aim Binds to a Complex I Subunit and Protects Mitochondrial Structure and Function," Antioxidants & Redox Signaling (2013) vol. 18, No. 16, pp. 2017-2028.

Olsson et al., "Up-Regulation of Al M/ ai-Microglobulin in Skin by Heme and Reactive Oxygen Species Gives Protection from Oxidative Damage," PLOS One (Nov. 2011) vol. 6, No. 11, pp. 1- 10.

Prise et al., "A Review of the Bystander Effect and Its Implications for Low-Dose Exposure," Radiation Protection Dosimetry (2003) vol. 104, No. 4, pp. 347-355.

Rutardottir et al., "The Cysteine 34 Residue of A1M/ $\alpha_1$-microglobulin is Essential for Protection of Irradiated Cell Cultures and Reduction of Carbonyl Groups," Free Radical Research (Jun.-Jul. 2013) vol. 47, Nos. 6-7, pp. 541-550.

Strober et al., "The Role of the Kidney in the Metabolism of Plasma Proteins," Nephron (1974) vol. 13, pp. 35-66.

Sverrisson et al., "Extracellular Fetal Hemoglobin Induces Increases in Glomerular Permeability: Inhibition with $\alpha_1$-Microglobulin and Tempol," Am. J. Physiol Renal Physiol (2014) vol. 306, pp. F442-F448.

Wester et al., "Physicochemical and Biochemical Characterization of Human $\alpha_1$-Microglobulin Expressed in Baculovirus-Infected Insect Cells," (1997) vol. 11, pp. 95-103.

Wester-Rosenlof et al., "A1M/ $\alpha_1$-Microglobulin Protects from Heme-Induced Placental and Renal Damage in a Pregnant Sheep Model of Preeclampsia," PLOS One (Jan. 2014) vol. 9, No. 1, pp. 1-12.

Zaknun et al., "The Joint IAEA, EANM, and SNMMI Practical Guidance on Peptide Receptor Radionuclide Therapy (PRRNT) in Neuroendocrine Tumours," Eur. J. Nucl. Med. Mol. Imaging (2013) vol. 40, pp. 800-816.

Katoh et al., "Protective Effect of Urinary Trypsin Inhibitor on the Development of Radiation-Induced Lung Fibrosis in Mice," *J. Radiat, Res.*, vol. 51, No. 3, pp. 325-332 (May 2010).

Wester-Rosenlof, et al., "A1M/a1-Microglubin Protects from Heme-Induced Placental and Renal Damage in a Pregnant Sheep Model od Preeclampsia," *PLOS One*, vol. 9, No. 1, 12 pages (Jan. 2014).

International Search Report issued in related International Patent Application No. PCT/EP2016/053904, dated May 12, 2016.

\* cited by examiner

Figure 12

SEQUENCE LISTING

<110> Åkerstrm, Bo
Hansson, Stefan

<120> Alpha-1-microglobulin for use in the protection of kidneys in radionuclide therapy

<130> P015472PCT1

<160> 4

<170> PatentIn version 3.5

<210> 1
<211> 183
<212> PRT
<213> Homo sapiens

<400> 1

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr

Figure 12 (Con't)

```
                115              120            125
Ala Lys Leu Tyr Gly Arg Ala Pro Gln Leu Arg Glu Thr Leu Leu Gln
    130             135             140

Asp Phe Arg Val Val Ala Gln Gly Val Gly Ile Pro Glu Asp Ser Ile
145             150             155             160

Phe Thr Met Ala Asp Arg Gly Glu Cys Val Pro Gly Glu Gln Glu Pro
            165             170             175

Glu Pro Ile Leu Ile Pro Arg
            180

<210> 2
<211> 201
<212> PRT
<213> Homo sapiens

<400> 2

Met His His His His His His His Gly Gly Gly Gly Gly Ile Glu
1               5              10              15

Gly Arg Gly Pro Val Pro Thr Pro Pro Asp Asn Ile Gln Val Gln Glu
        20              25              30

Asn Phe Asn Ile Ser Arg Ile Tyr Gly Lys Trp Tyr Asn Leu Ala Ile
        35              40              45

Gly Ser Thr Cys Pro Trp Leu Lys Lys Ile Met Asp Arg Met Thr Val
    50              55              60

Ser Thr Leu Val Leu Gly Glu Gly Ala Thr Glu Ala Glu Ile Ser Met
65              70              75              80

Thr Ser Thr Arg Trp Arg Lys Gly Val Cys Glu Glu Thr Ser Gly Ala
            85              90              95

Tyr Glu Lys Thr Asp Thr Asp Gly Lys Phe Leu Tyr His Lys Ser Lys
            100             105             110
```

Figure 12 (Con't)

```
Trp Asn Ile Thr Met Glu Ser Tyr Val Val His Thr Asn Tyr Asp Glu
    115             120             125

Tyr Ala Ile Phe Leu Thr Lys Lys Phe Ser Arg His His Gly Pro Thr
    130             135             140

Ile Thr Ala Lys Leu Tyr Gly Arg Ala Pro Gln Leu Arg Glu Thr Leu
145             150             155             160

Leu Gln Asp Phe Arg Val Val Ala Gln Gly Val Gly Ile Pro Glu Asp
          165             170             175

Ser Ile Phe Thr Met Ala Asp Arg Gly Glu Cys Val Pro Gly Glu Gln
      180             185             190

Glu Pro Glu Pro Ile Leu Ile Pro Arg
      195             200

<210> 3
<211> 549
<212> DNA
<213> Homo sapiens

<400> 3
ggccctgtgc caacgccgcc cgacaacatc caagtgcagg aaaacttcaa tatctctcgg      60
atctatggga agtggtacaa cctggccatc ggttccacct gcccctggct gaagaagatc     120
atggacagga tgacagtgag cacgctggtg ctgggagagg gcgctacaga ggcggagatc     180
agcatgacca gcactcgttg gcggaaaggt gtctgtgagg agacgtctgg agcttatgag     240
aaaacagata ctgatgggag gtttctctat cacaaatcca atggaacat  aaccatggag     300 tcctatgtgg tccacaccac ctatgatgag tatgccattt ttctgaccaa gaaattcagc     360
cgccatcatg gacccaccat tactgccaag ctctacgggc gggcgccgca gctgagggaa     420
actctcctgc aggacttcag agtggttgcc cagggtgtgg gcatccctga ggactccatc     480
ttcaccatgg ctgaccgagg tgaatgtgtc cctggggagc aggaaccaga gcccatctta     540
atcccgaga                                                            549

<210> 4
```

Figure 12 (Con't)

<211> 603
<212> DNA
<213> Homo sapiens

<400> 4

| | | | | |
|---|---|---|---|---|
| atgcatcacc | atcaccatca | ccatcacggt | ggaggagggg | gtatcgaggg ccgcggccct | 60 |
| gtgccaacgc | cgcccgacaa | catccaagtg | caggaaaact | tcaatatctc tcggatctat | 120 |
| gggaagtggt | acaacctggc | catcggttcc | acctgcccct | ggctgaagaa gatcatggac | 180 |
| aggatgacag | tgagcacgct | ggtgctggga | gagggcgcta | cagaggcgga gatcagcatg | 240 |
| accagcactc | gttggcggaa | aggtgtctgt | gaggagacgt | ctggagctta tgagaaaaca | 300 |
| gatactgatg | ggaggttttct | ctatcacaaa | tccaaatgga | acataaccat ggagtcctat | 360 |
| gtggtccaca | ccacctatga | tgagtatgcc | attttctga | ccaagaaatt cagccgccat | 420 |
| catggaccca | ccattactgc | caagctctac | gggcgggcgc | cgcagctgag ggaaactctc | 480 |
| ctgcaggact | tcagagtggt | tgcccagggt | gtgggcatcc | ctgaggactc catcttcacc | 540 |
| atggctgacc | gaggtgaatg | tgtccctggg | gagcaggaac | cagagcccat cttaatcccg | 600 |
| aga | | | | | 603 |

ALPHA-1-MICROGLOBULIN FOR USE IN THE PROTECTION OF KIDNEYS IN RADIONUCLIDE THERAPY

CROSS-REFERENCE RELATED APPLICATIONS

The present application is the U.S. National Stage of International Application No. PCT/EP2016/053904, filed Feb. 25, 2016, and claims priority to Denmark Patent Application No. PA 2015 70099, filed Feb. 25, 2015.

SEQUENCE LISTING

The present application contains a Sequence Listing which has been submitted electronically in ASCII format and is hereby incorporated by reference in its entirety.

FIELD OF THE INVENTION

The present invention relates to the use of alpha-1-microglobulin (A1M) for reducing the kidney-related side-effects observed in radionuclide diagnostics (RD), radionuclide therapy (RNT) and radioimmunotherapy (RIT) during treatment of malignancies such as neuroendocrine tumours with small molecules labelled with radionuclides. The small molecules include receptor ligands (c.f. somatostatin derivatives), Affibodies, Diabodies and antibody fragments (Fab, Fv, scFv, etc).

Moreover, the invention relates to the use of A1M in the treatment of acute and/or chronic kidney injuries.

BACKGROUND OF THE INVENTION

For the past 15 years peptide receptor radionuclide therapy (PRRT) has been used to successfully treat metastatic neuroendocrine tumors [1]. Somatostatin-analogous peptides such as octreotide, labelled with therapeutic radionuclides, are used to treat somatostatin receptor-positive tumors [2]. However, renal toxicity and chronic kidney insufficiency are typical side effects of PRRT. Despite protective measures such as infusion of positively charged amino acids, a delayed loss of renal function has been observed in patients undergoing PRRT due to proximal tubular reabsorption and retention in the interstitium [1]. Therefore, the kidneys are dose-limiting organs in PRRT. It has been observed that patients treated with $^{177}$Lu-DOTATATE suffered a creatinine clearance loss of 3.8% per year, and 7.3% a year for patients treated with $^{90}$Y-DOTA-TOC [3]. Another approach for therapy using small molecular candidates is Affibody molecules, Diabodies and fragments of antibodies and immunoconjugates (i.e. Fab, scFv, etc). Those have been shown in both pre-clinical and clinical studies to have high kidney accumulation with associated high kidney radioactivity.

The problems with renal toxicity have not been sufficiently solved and there is still a need to identify or develop means that increase the safety of using PRRT and reduce associated organ toxicity. Furthermore, also during repeated radionuclide diagnostics (radionuclide imaging), the ALATA (As Low As Reasonably Achievable) principle would benefit from developing means to reduce the biological effect from ionizing radiations.

DETAILED DESCRIPTION OF THE INVENTION

Peptide-receptor radionuclide therapy (PRRT) is in clinical use for treatment of neuroendocrine tumors. Renal toxicity due to glomerular filtration of the peptides followed by local radiation and generation of radicals is a side-effect that limits the dosage and usefulness of the method. $\alpha_1$-microglobulin (A1M) is a human radical-scavenging protein shown to prevent radiation-induced in vitro cell damage and damage to surrounding cells. A1M is synthesized in the liver, secreted to the blood, equilibrated to the extravascular compartments and filtrated in the kidneys.

Aiming to develop A1M-based therapy against renal toxic side-effects of PRRT the inventors have, as a first proof of concept, compared the kinetics and biodistribution in mice of injected recombinant A1M and the somatostatin analogue octreotide. Both molecules were localized predominantly to the kidneys with a more rapid kinetics of A1M compared to octreotide. A maximum of 76% of injected A1M and 46% of injected octreotide were found per gram kidney tissue at 10 and 20 minutes, respectively, after i.v. injection. Importantly, the A1M molecule was shown to be intact, full-length at least up to 60 minutes post-injection. Autoradiography of the kidneys showed that the labelled A1M and octreotide were mainly localized to the cortex after 10-60 minutes. Immunohistochemistry and fluorescence microscopy revealed a co-localization of the two substances mainly to the lumen and epithelial cells of the proximal tubules. The results show a highly similar pharmacokinetics and biodistribution of A1M and octreotide, thus enabling the use of A1M to protect the kidneys tissue during PRRT.

In accordance with the results reported herein and briefly mentioned above, the present invention relates to A1M and PRRN (peptide receptor radiation nuclide) for use in combination in radionuclide therapy.

More specifically, the invention relates to:

$\alpha_1$-microglobulin (A1M) for use in the treatment of malignancies requiring radionuclide therapy (RNT) or radioimmunotherapy (RIT), wherein A1M is used as a co-treatment to RNT or RIT;

A1M and a compound labeled with radionuclide for use in the treatment of malignancies requiring radionuclide therapy (RNT) or radioimmunotherapy (RIT);

A1M for use in the treatment of kidney injuries.

A1M for use in reducing the unwanted biological effect from ionizing radiation during radionuclide diagnostics (nuclear medicine imaging) in single or multiple imaging sessions. A1M is used to achieve the ALARA principle and reduce the unwanted effect of ionizing radiation to the patient.

As described below, the compound labeled with radionuclide is selected from the group consisting of peptide receptor ligand, Affibodies and antibody fragments. The compound labeled with radionuclide is a peptide coupled to a radionuclide emitting radiation.

PRRT is a form of molecular targeted therapy, which is performed by use of a small peptide coupled to a radionuclide emitting radiation. The small peptides are somatostatin analogues. Such analogues include octreotide, lanreotide, Tyr$^3$-octreotide (TOC), Tyr$^3$-octrotate (TATE) and the DOTA$^+$-chelates DOTADOC, DODATATE and DOTA-lanreotide. Other somatostatin analogues include SOM230 (pasireotide), dopastatin and octreotide LAR. The somatostatin analogues are labelled with radionuclides emitting medium and/or high energy beta particles such as Yttrium-90 ($^{90}$Y) or Lutetium-177 ($^{177}$Lu) and administered to the patient intravenously (i.v.). The therapy is conducted on patients having somatostatin receptor positive tumors. Many, but not all, forms for neuroendocrine tumors (NETs) express one or more somatostatin receptor subtype. After administration of a PRRN it binds to the somatostatin receptor localized on the tumor and the PRRN is retained in the tumor. The decay of the radionuclide emitting ionizing radiation deposits energy in the tissues resulting in a high absorbed dose.

In the present context the invention is not limited to a specific PRRN such as those mentioned above, but any molecule labelled with any suitable radionuclide capable of emitting ionizing radiation is intended to be within the scope of the present invention, such as the radionuclide-labelled small molecules Affibody molecules, Diabodies, Fab, Fv, scFv-fragments and other immunoconjugates or other receptor ligands. It is preferred that the PRRN selected is distributed to the kidney with a comparable kinetics as A1M in order to achieve optimal protective effect of A1M.

As mentioned above one of the therapies where A1M would be useful is in the treatment of neuroendocrine tumors. Neuroendocrine tumors (NETs) comprise a heterogeneous group of cancers that often remain asymptomatic until the primary tumor has metastasized.

Other therapies are those, which may lead to kidney injury. Such therapies include treatment of streptococcal infection, *E. coli*-infection (eHUS), autoimmunity (SLE), diabetes etc.

In any event it is contemplated that A1M has a protective effect on kidney tissue.

Neuroendocrine tumors are neoplasms that arise from cells of the endocrine and nervous system. This type of tumors include gastroenteropancreatic tumors (so-called DEP-NETs) eg arising from the small bowel, duodenum, stomach, or pancreas, but also from the large bowel or the lung or many other tissues. Neuroendocrine tumors occurring in the intestines are also called carcinoid tumors.

Once the cancer has spread, the treatment becomes difficult and surgical resection is difficult or unlikely. Several treatment options exist to treat advanced NETs including surgery, somatostatin analogues, chemotherapy etc., although most of these are suboptimal for complete remission. The choice of therapy is determined by the stage of the disease and the size and aggressiveness of the tumor.

PRRT seems to be highly effective in controlling progressive NETs. Although complete response rates are relatively low, the percentage of patients with partial remission and stable disease following treatment is high.

As described above, however, the PRRT treatment option is limited by renal reabsorption and retention of radiolabelled peptide resulting in dose-limiting kidney radiotoxicity. Radiation nephropathy has been described in several patients. In order to achieve kidney protection PRRN has been co-administered with positively charged amino acids, a bovine-gelatin solution (Gelofusine) or albumin fragments. No optimal solution has been found yet, however.

Radionuclide tumour therapy mechanisms include cell death (necrosis and apoptosis) in the targeted tissues, but also various forms of non-lethal stress to living cells, including "oxidative stress." Oxidative stress is induced by ionization of solvent and cell components, and secondary oxidative stress by induced cell necrosis from ionizing radiation. Oxidative stress is defined as increased tissue oxidation due to an imbalance between the generation of oxidative compounds and the detoxification of oxidants/ repair of oxidized tissue [4]. Major mediators of oxidative stress are reactive oxygen species (ROS). ROS and free radicals react with proteins, DNA and other molecular components to cause oxidation of human cells and tissues, which leads to unwanted modifications of the target molecules, loss of function and cell death. Necrosis induces oxidative stress mainly by disrupting the compartmentalization of oxidative processes. During radionuclide therapy, a "bystander effect" can be observed, i.e. a stress-response in which cells that are not directly exposed to the irradiation suffer indirect damage. The bystander effect is induced by a propagation of stress factors from the cells irradiated directly and manifests as cell death, genomic instability and changes in gene expression in the non-irradiated bystander cells [4-7]. Oxidants and ROS have been suggested as mediators of the bystander effects [8-10].

Antioxidants are protective factors that eliminate oxidants or prevent harmful oxidation reactions [4]. The human organism can produce antioxidants in response to oxidative stress. Such endogenous antioxidants include the superoxide-degrading enzyme superoxide dismutase (SOD), the hydrogen peroxide-degrading enzymes catalase and glutathione peroxidase, and the heme-degrading enzyme heme oxygenase-1 (HO-1). A normally occurring 26 kDa plasma and tissue protein, $\alpha_1$-microglobulin (A1M), was recently shown to be involved in protecting against oxidative tissue damage by functioning both as a scavenger of radicals and heme as well as a reductase and inhibitor of oxidation [11-15]. Several recent papers demonstrate that A1M protects cell cultures and organ explants against oxidative damage [16-18], partly by accumulating in mitochondria and protecting mitochondrial function [19]. Indeed, infusion of human recombinant A1M has been successfully employed for in vivo treatment of the oxidative stress-related diseases preeclampsia [20] and hemoglobin-induced glomerular injuries [21] in animal models. Of particular interest in this invention, A1M has been shown to suppress the cell death, apoptosis, and up-regulation of stress-response genes in the bystander cells of irradiated cell cultures [22,23].

Based on pharmacokinetic studies, the present inventors have found that A1M and a somatostatin analogue-based PRRN both are quickly distributed to the kidney after administration. A prerequisite for a protective action of A1M is that the protein is not degraded immediately after its localization to the kidneys. As demonstrated in the examples herein a majority of A1M found in the kidneys was still intact at least 60 minutes after i.v. injection. Thus, A1M can exert a protective effect against kidney damages caused by PRRT.

The inventors have shown that >30% of i.v. administered $^{125}$I-labelled A1M was localized in kidneys within a few minutes. Based on the inventors' observations, and the shown protective properties of the A1M against radiation induced tissue damage, the present inventors propose to use A1M-infusion as a method to improve PRRT by reducing kidney toxicity. A prerequisite for such an A1M-based method is a high degree of co-localization of therapeutic A1M and octreotide. In the experimental section herein, the kinetics and biodistribution of recombinant human A1M and octreotide were investigated on the organ and cellular levels.

In order to evaluate whether infusion of therapeutic A1M would be able to protect against the side effects observed in patients undergoing PRRT, it is of importance to study and compare the kinetics and distribution of A1M with somatostatin analogues used in therapy of these tumors. The degree of co-localization of these molecules, on both the organ and cellular level, is of special interest and was thoroughly investigated as reported in the experimental section herein using several imaging techniques.

The biodistribution studies performed showed a high specific uptake in the kidneys for both molecules with a maximum uptake 10 and 20 minutes, post-injection for A1M and octreotide respectively, and with overlapping kinetics during the clearance phase (FIG. 1). This suggests that any protective A1M infusion should be done at the same time, or shortly after the octreotide injections. The rapid clearance of A1M from the kidneys also suggests that several infusions of A1M may be needed in order to fully protect the kidneys.

Mirroring the biodistribution results, non-invasive SPECT imaging shows high uptake in the kidneys for both molecules. A higher concentration of both octreotide and A1M can be observed in the kidney cortex as compared to the medulla, suggesting co-localization in these regions already after 20 minutes.

A prerequisite for a protective action of A1M is of course that the protein is not degraded immediately after its localization in the kidneys. The inventors therefore investigated the size of the protein in kidney homogenates. As evident from FIG. 2, the majority of A1M found in the kidneys display full-length size at least up to 60 minutes post-injection. A natural route of A1M in the kidneys, similar to most small plasma proteins, is glomerular filtration from blood to the primary urine, followed by reabsorption and lysosomal degradation in the proximal tubular epithelium [29,30]. A small fraction of A1M can still be found in urine [24]. It can therefore be speculated that although a large part is expected to be degraded in the proximal tubular cells, a significant amount of A1M may escape tubular reabsorption and degradation and is left intact and functional during the first 10-60 min.

$\alpha_1$-Microglobulin—a General Background

A1M is synthesized in the liver at a high rate, secreted into the blood stream and transported across the vessel walls to the extravascular compartment of all organs. The protein is also synthesized in other tissues (blood cells, brain, kidney, skin) but at a lower rate. Due to the small size, free A1M is rapidly filtered from blood in the kidneys.

Figure 3:
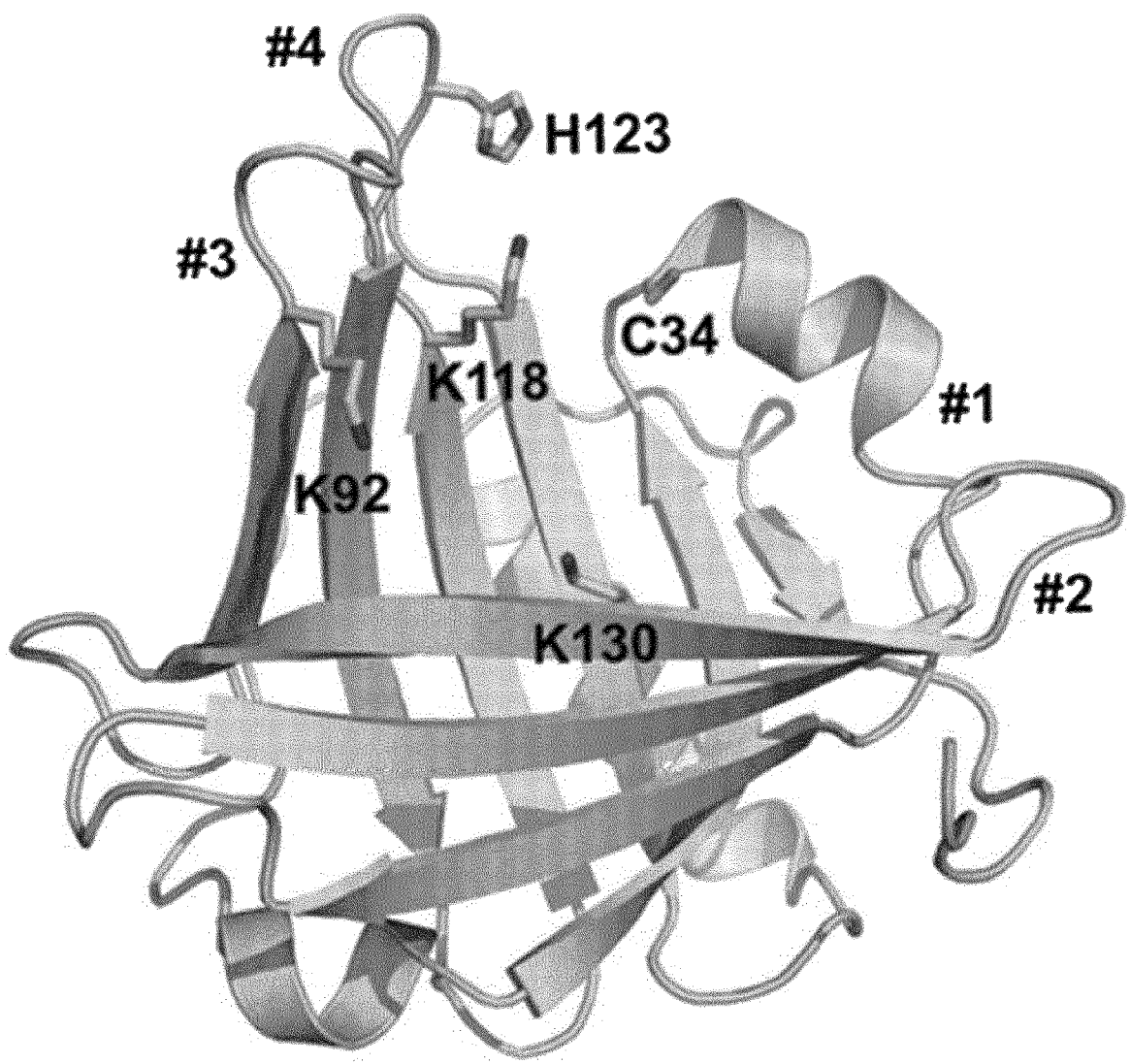

A1M is a member of the lipocalin superfamily, a group of proteins from animals, plants and bacteria with a conserved three-dimensional structure but very diverse functions. Each lipocalin consists of a 160-190-amino acid chain that is folded into a $\beta$-barrel pocket with a hydrophobic interior. At least twelve human lipocalin genes are known. A1M is a 26 kDa plasma and tissue protein that so far has been identified in mammals, birds, fish and frogs. The three-dimensional structure of A1M determined by X-ray crystallography is shown in FIG. 3. A1M is synthesized in the liver at a high rate, secreted into the blood stream and rapidly (T½=2-3 min) transported across the vessel walls to the extravascular compartment of all organs. A1M is found both in a free, monomeric form and as covalent complexes with larger molecules (IgA, albumin, prothrombin) in blood and interstitial tissues. Due to the small size, free A1M is rapidly filtered from blood in the kidneys. The major portion is then readsorbed, but significant amounts are excreted to the urine.

Sequence and Structural Properties of A1M

The full sequence of human A1M is known. The protein consists of a polypeptide with 183 amino acid residues. Many additional A1M cDNAs and/or proteins have been detected, isolated and/or sequenced from other mammals, birds, amphibians, and fish. The length of the peptide chain of A1M differs slightly among species, due mainly to variations in the C-terminus. Alignment comparisons of the different deduced amino acid sequences show that the percentage of identity varies from approximately 75-80% between rodents or ferungulates and man, down to approximately 45% between fish and mammals. A free cysteine side-chain at position 34 is conserved. This group has been shown to be involved in redox reactions (see below), in complex formation with other plasma proteins and in binding to a yellow-brown chromophore. The three-dimensional structure of A1M shows that C34 is solvent exposed and located near the opening of the lipocalin pocket (see FIG. 3).

In the present context the term "$\alpha_1$-microglobulin" intends to cover $\alpha_1$-microglobulin as identified in SEQ ID NO: 1 (human A1M) as well as SEQ ID NO: 2 (human recombinant A1M) as well as homologues, fragments or variants thereof having similar therapeutic activities. Thus, A1M as used herein is intended to mean a protein having at least 80% sequence identity with SEQ ID NO:1 or SEQ ID NO:2. It is preferred that A1M as used herein has at least 90% sequence identity with SEQ ID NO:1 or SEQ ID NO:2. It is even more preferred that A1M as used herein has at least 95% such as 99% or 100% sequence identity with SEQ ID NO:1 or SEQ ID NO:2. In a preferred aspect, the $\alpha_1$-microglobulin is in accordance with SEQ ID NO: 1 or 2 as identified herein. In FIG. 12 is given the sequence listing of the amino acid sequence of human A1M and human recombinant A1M (SEQ ID NOs 1 and 2, respectively) and the corresponding nucleotide sequences (SEQ ID NOs 3 and 4, respectively). However, homologues, variants and fragments of A1M having the important parts of the proteins as identified in the following are also comprised in the term A1M as used herein.

As mentioned above homologues of A1M can also be used in accordance with the description herein. In theory A1M from all species can be used for the purposes described herein including the most primitive found so far, which is from fish (plaice). A1M is also available in isolated form from human, orangutan, squirrel monkey, rat, naked mole rat, mouse, rabbit, guinea pig, cow, frog, chicken, walrus, manatee and plaice.

It is important to note that even if A1M and bikunin have the same precursor, they have different amino acid compositions and have different properties. A1M belongs to the so-called lipocalin family whereas bikunin (also denoted ulinastatin) belongs to the protease inhibitor superfamily.

Considering homologues, variants and fragments of A1M, the following has been identified as important parts of the protein for the anti-oxidative effect:

Y22 (Tyrosine, pos 22, basepairs 64-66)
C34 (Cystein, position 34, basepairs 100-102)
K69 (Lysine, pos 69, basepairs 205-207)
K92 (Lysine, pos 92, basepairs 274-276)
K118 (Lysine, pos 118, basepairs 352-354)
K130 (Lysine, pos 130, basepairs 388-390)
Y132 (Tyrosine, pos 132, basepairs 394-396)
L180 (Leucine, pos 180, basepairs 538-540)
I181 (Isoleucine, pos 181, basepairs 541-543)
P182 (Proline, pos 182, basepairs 544-546)
R183 (Arginine, pos 183, basepairs 547-549)

Figure 4:
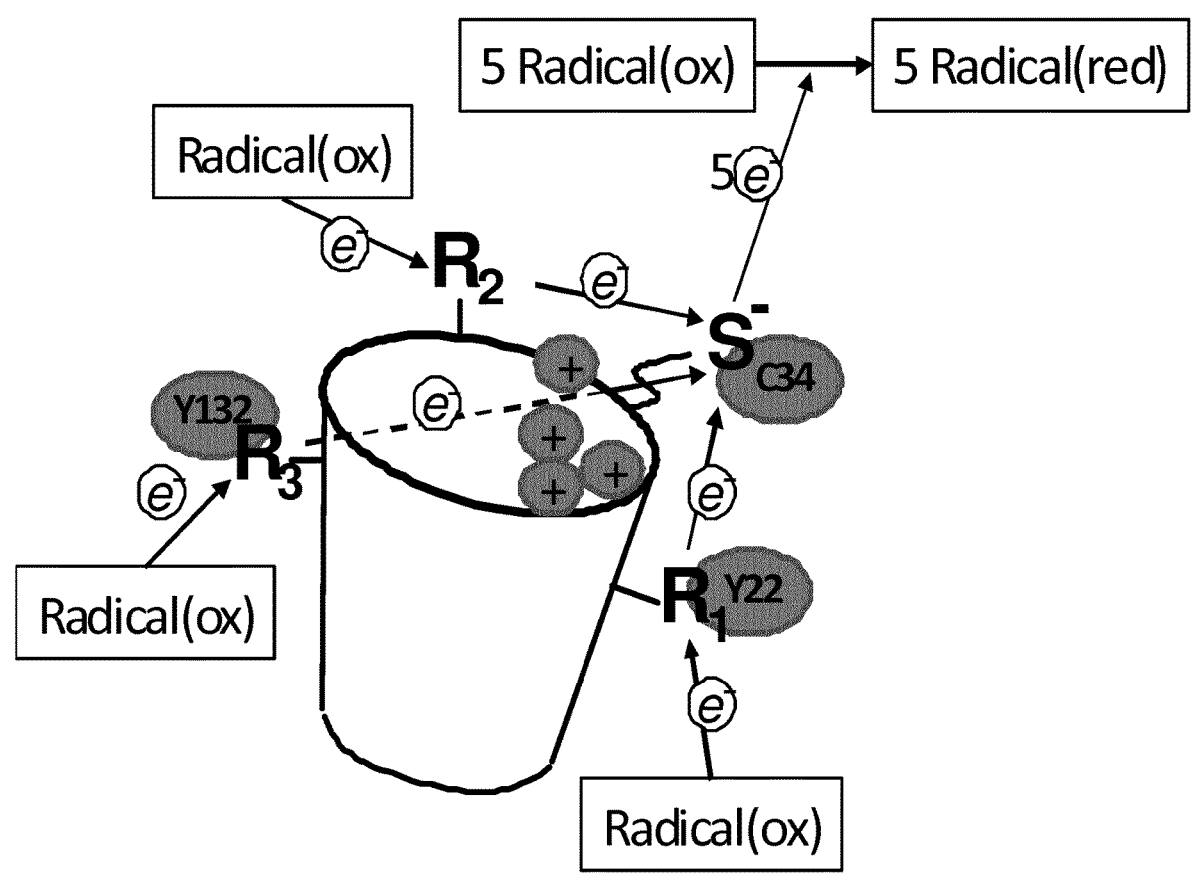

(Numbering of amino acids and nucleotides throughout the document refers to SEQ ID 1 and 3, see also FIGS. 3 and 4; if other A1M from other species, A1M analogs or recombinant sequences thereof are employed, a person skilled in the art will know how to identify the amino acids of the active site(s) or site(s) responsible for the enzymatic activity.)

Thus, in those cases, where A1M eg has 80% (or 90% or 95%) sequence identity with one of SEQ ID NO: 1 or 2, it is preferred that the amino acids mentioned above are present at the appropriate places in the molecule.

Human A1M is substituted with oligosaccharides in three positions, two sialylated complex-type, probably diantennary carbohydrated linked to N17 and N96 and one more simple oligosaccharide linked to T5. The carbohydrate content of A1M proteins from different species varies greatly, though, ranging from no glycosylation at all in *Xenopus*

*leavis* over a spectrum of different glycosylation patterns. However, one glycosylation site, corresponding to N96 in man, is conserved in mammals, suggesting that this specific carbohydrate may be functionally important.

A1M is yellow-brown-coloured when purified from plasma or urine. The colour is caused by heterogeneous compounds covalently bound to various amino acid side groups mainly located at the entrance to the pocket. These modifications represent the oxidized degradation products of organic oxidants covalently trapped by A1M in vivo, for example heme, kynurenine and tyrosyl radicals.

A1M is also charge- and size-heterogeneous and more highly brown-coloured A1M-molecules are more negatively charged. The probable explanation for the heterogeneity is that different side-groups are modified to a varying degree with different radicals, and that the modifications alter the net charge of the protein. Covalently linked coloured substances have been localized to C34, and K92, K118 and K130, the latter with molecular masses between 100 and 300 Da. The tryptophan metabolite kynurenine was found covalently attached to lysyl residues in A1M from urine of haemodialysis patients and appears to be the source of the brown colour of the protein in this case [6]. Oxidized fragments of the synthetic radical ABTS (2,2'-azino-di-(3-ethylbenzothiazoline)-6-sulfonic acid) was bound to the side-chains of Y22 and Y132.

C34 is the reactive center of A1M. It becomes very electronegative, meaning that it has a high potential to give away electrons, by the proximity of the positively charged side-chains of K69, K92, K118 and K130, which induce a deprotonization of the C34 thiol group which is a prerequisite of oxidation of the sulphur atom. Preliminary data shows that C34 is one of the most electronegative groups known.

Theoretically, the amino acids that characterize the properties of A1M (C34, Y22, K92, K118, K130, Y132, L180, I181, P182, R183), which will be described in more detail below, can be arranged in a similar three-dimensional configuration on another framework, for instance a protein with the same global folding (another lipocalin) or a completely artificial organic or inorganic molecule such as a plastic polymer, a nanoparticle or metal polymer.

The three-dimensional arrangement of some of these amino acids (blue ovals, the lysines are depicted by a "+"), the A1M-framework (barrel), the electron-flow and the radical-trapping, are illustrated in FIG. 4.

Accordingly, homologues, fragments or variants comprising a structure including the reactive centre and its surroundings as depicted above, are preferred.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity.

Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids the hydrophilicity values of which are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln$_1$ His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Lle, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

In the present context, the homology between two amino acid sequences or between two nucleic acid sequences is described by the parameter "identity". Alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6.

Multiple alignments of protein sequences may be made using "ClustalW". Multiple alignments of DNA sequences may be done using the protein alignment as a template, replacing the amino acids with the corresponding codon from the DNA sequence.

Alternatively different software can be used for aligning amino acid sequences and DNA sequences. The alignment of two amino acid sequences is e.g. determined by using the Needle program from the EMBOSS package (emboss.org) version 2.8.0. The Needle program implements the global alignment algorithm described in. The substitution matrix used is BLOSUM62, gap opening penalty is 10, and gap extension penalty is 0.5.

The degree of identity between an amino acid sequence; e.g. SEQ ID NO: 1 and a different amino acid sequence (e.g. SEQ ID NO: 2) is calculated as the number of exact matches in an alignment of the two sequences, divided by the length of the "SEQ ID NO: 1" or the length of the "SEQ ID NO: 2", whichever is the shortest. The result is expressed in percent identity.

An exact match occurs when the two sequences have identical amino acid residues in the same positions of the overlap.

If relevant, the degree of identity between two nucleotide sequences can be determined by the Wilbur-Lipman method using the LASER-GENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

The percentage of identity of an amino acid sequence of a polypeptide with, or to, amino acids of SEQ ID NO: 1 may be determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention is calculated in an analogous way.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylpróline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. In a second method, translation is carried out in Xenopus oocytes by microinjection of mutated mRNA and chemically aminoacylated suppressor tRNAs. Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. Naturally occurring amino acid residues can be converted to non-naturally occurring species by in vitro chemical modification. Chemical modification can be combined with site-directed mutagenesis to further expand the range of substitutions. Alternative chemical structures providing a 3-dimensional structure sufficient to support the antioxidative properties of A1M may be provided by other technologies e.g. artificial scaffolds, amino-acid substitutions and the like. Furthermore, structures mimicking the active sites of A1M as listed above and depicted in FIGS. 3 and 4 are contemplated as having the same function as A1M.

Pharmaceutical Compositions and Dosage

The present invention also provides a kit comprising:
i) a pharmaceutical composition comprising a PRRN, and
ii) a pharmaceutical composition comprising A1M.

The kit is in the form of one package containing the above-mentioned two compositions.

The pharmaceutical composition comprising PRRN is typically a composition already on the market.

The pharmaceutical composition comprising A1M (or an analogue, fragment or variant thereof as defined herein) is intended for i.v. administration. Accordingly, A1M can be formulated in a liquid, e.g. in a solution, a dispersion, an emulsion, a suspension etc. As it appears from the examples herein a suitable vehicle for i.v. administration may be composed of 10 mM Tris-HCl, pH 8.0 and 9.125 M NaCl.

For parenteral use suitable solvents include water, vegetable oils, propylene glycol and organic solvents generally approved for such purposes. In general, a person skilled in the art can find guidance in "Remington's Pharmaceutical Science" edited by Gennaro et al. (Mack Publishing Company), in "Handbook of Pharmaceutical Excipients" edited by Rowe et al. (PhP Press) and in official Monographs (e.g. Ph.Eur. or USP) relating to relevant excipients for specific formulation types and to methods for preparing a specific formulation.

A1M will be administrated in one or several doses in connection to the radionuclide therapy dose. Preferably, each dose will be administrated i.v. either as a single dose, as a single dose followed by slow infusion during a short time-period up to 60 minutes, or only as a slow infusion during a short time-period up to 60 minutes. The first dose will be administrated at the same time as the radionuclide therapy peptide, or within a period of 0-60 minutes before to 0-30 minutes after injection of the radionuclide dose. Additional A1M-doses can be added, but may not be necessary, after injection of the radionuclide treatment dose. Each dose contains an amount of A1M which is related to the bodyweight of the patient: 1-15 mg A1M/kg of the patient. In the study described in the examples herein a dose of 7 mg/kg (mouse model) is employed.

BRIEF DESCRIPTION THE DRAWINGS

FIG. 1 shows the biodistribution of $^{125}$I-A1M (upper left) and $^{111}$In-Octreotide (upper right) in normal NMRI mice. Lower left image shows uptake over time for both molecules in the kidneys. Data are presented as % IA/g from 4 animals±SEM.

Figure 2:
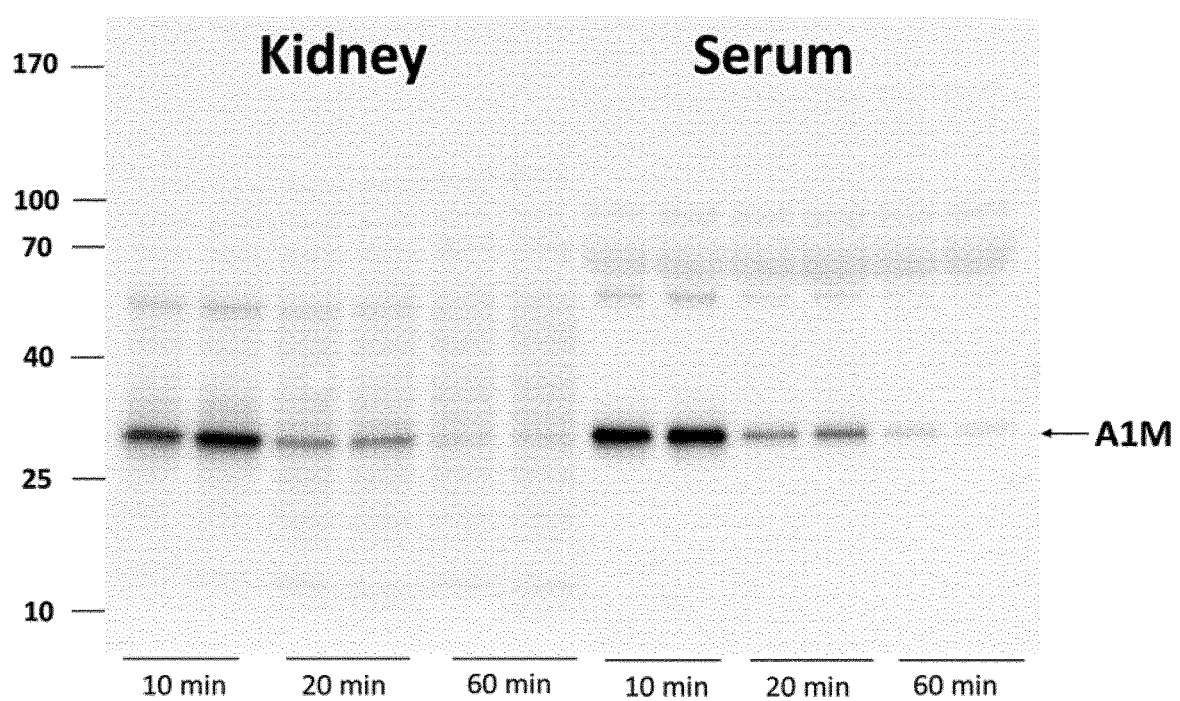

FIG. 2 shows the presence of full-length A1M in normal NMRI mice in kidneys and serum at 10, 20 and 60 minutes post-injection. Animals were injected i.v. with 150 µg A1M and blood and kidneys collected at the indicated time-points. The blood was allowed to coagulate and serum separated by centrifugation. One kidney was homogenized in 1 ml PBS and centrifuged. 1 µl serum and 6 µl supernatant from the kidney homogenate were applied to SDS-PAGE, transferred to PVDF-membranes and blotted with anti-A1M. Each lane represents a separate mouse.

FIG. 3 shows the three-dimensional structure of A1M. The illustration was generated using PyMOL [Molinspiration, M. v. (2014)] and coordinates from the crystal structure of human A1M [Meining, W., and Skerra, A. (2012) The crystal structure of human $\alpha_1$-microglobulin reveals a potential haem-binding site. Biochem J 445, 175-182]. β-strands and α-helices are shown in green ribbons. Side-chains of C34, K92, K118, K130 and H123, involved in functional activities of A1M, are shown as green sticks with nitrogen atoms in blue. The four lipocalin loops are labeled #1-#4.

FIG. 4 shows the three-dimensional arrangement of some amino acids (blue ovals, the lysines are depicted by a "+"), the A1M-framework (barrel), the electron-flow and the radical-trapping.

Figure 5:
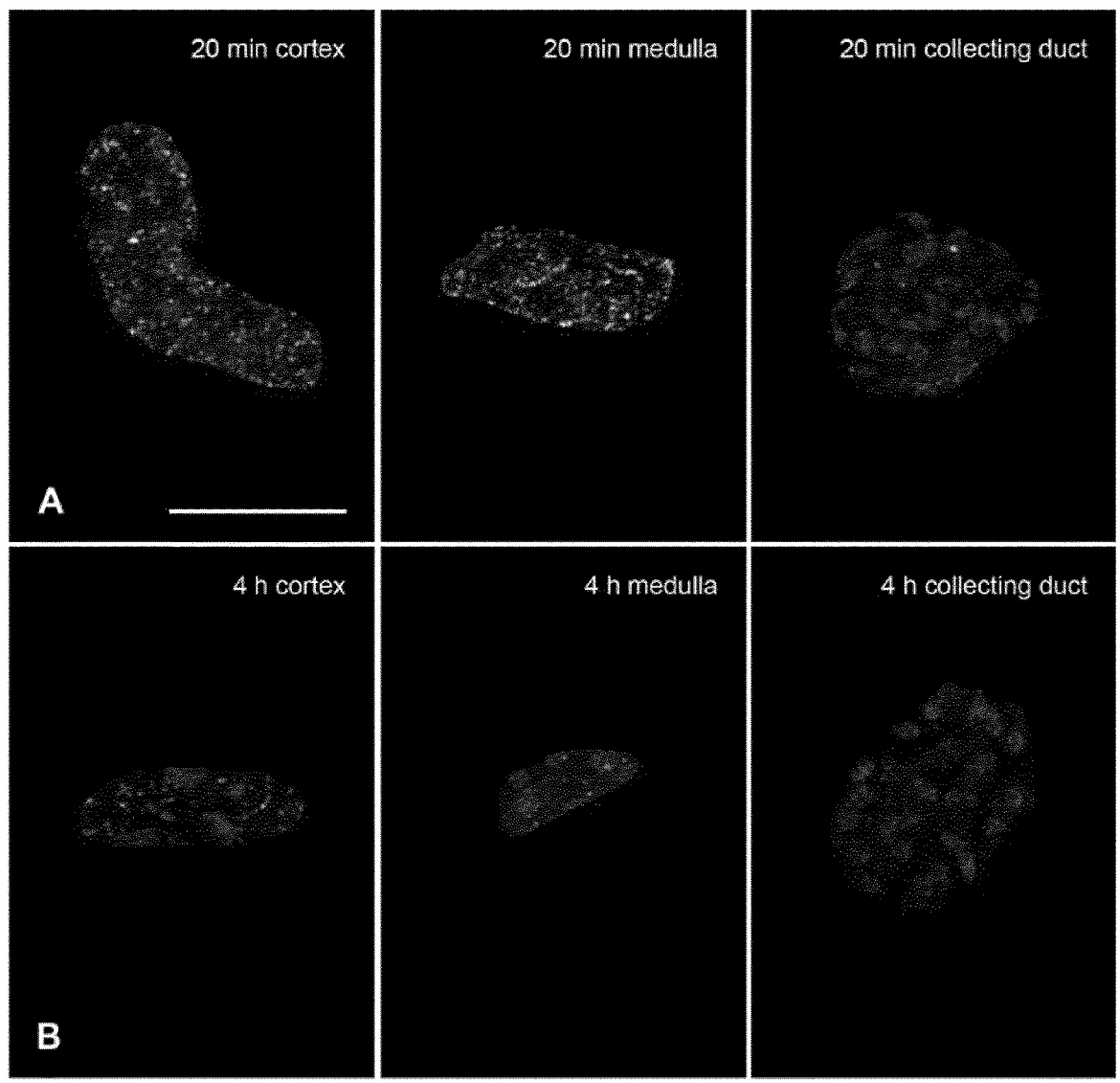
Figure 5:
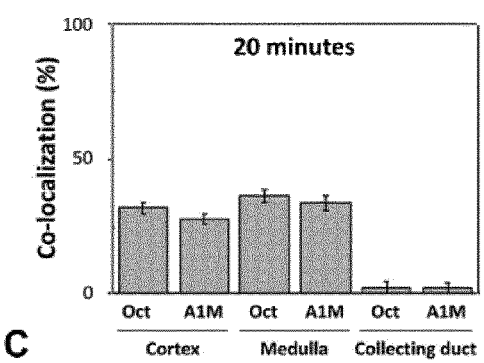
Figure 5:
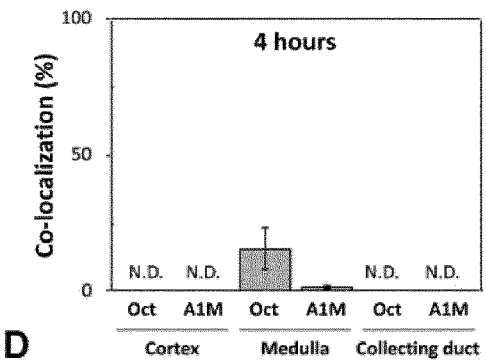
Figure 5:
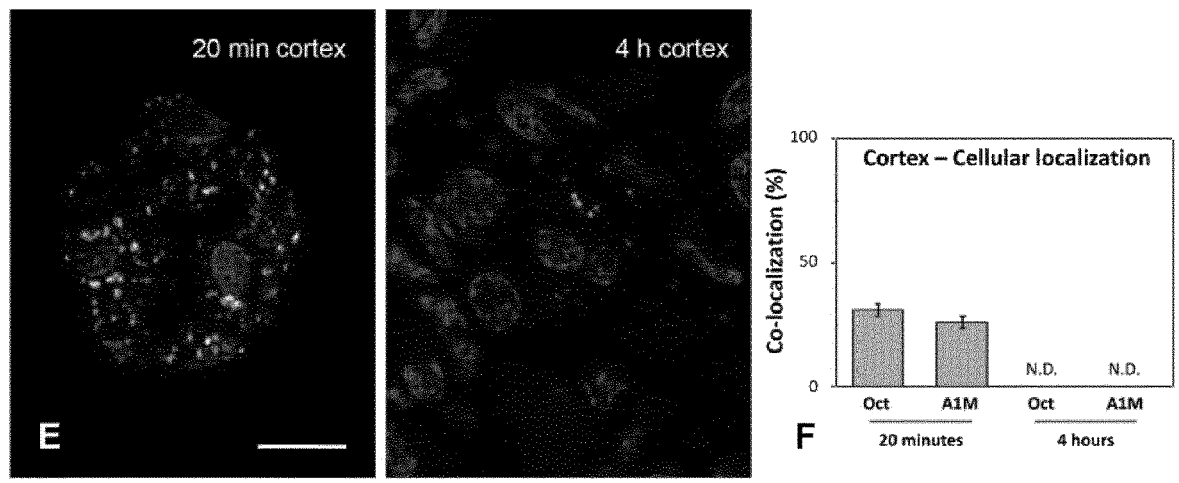

FIG. 5 A-D show tubular localization of A1M and Octreotide-A647 at different post-injection times. A1M and Octreotide-A647 conjugate were injected i.v. and animals were terminated at 20 minutes (A, C) and 4 hours (B, D) following injection. The percentage of co-localized A1M (green) and Octreotide-A647 (red) was measured in selected tubular profiles in the cortex, medulla and collecting ducts, in confocal microscopic images (20×/0.8 objective). Cell nuclei were visualized using DAPI (blue). Representative profiles (A, B) show different degrees of co-localization (yellow), and the co-localization data from all investigated samples are presented as mean±SEM of representative areas (C, D). Scale bar represents 50 µm.

FIGS. 5 E-F show cellular co-localization of A1M and Octreotide-A647 at different post-injection times. A1M and Octreotide-A647 conjugate were injected i.v. and animals were terminated at 20 minutes and 4 hours (E, left and right) following injection. The percentage of co-localized A1M (green) and Octreotide-A647 (red) was measured in selected tubular profiles in the cortex, in high-resolution confocal microscopic images (63×/1.4 objective). Cell nuclei were visualized using DAPI (blue). Representative profiles (E) show different degrees of intracellular co-localization (yellow), and the co-localization data from all investigated samples are presented as mean±SEM of representative areas (F). Scale bar represents 20 µm.

Figure 6:
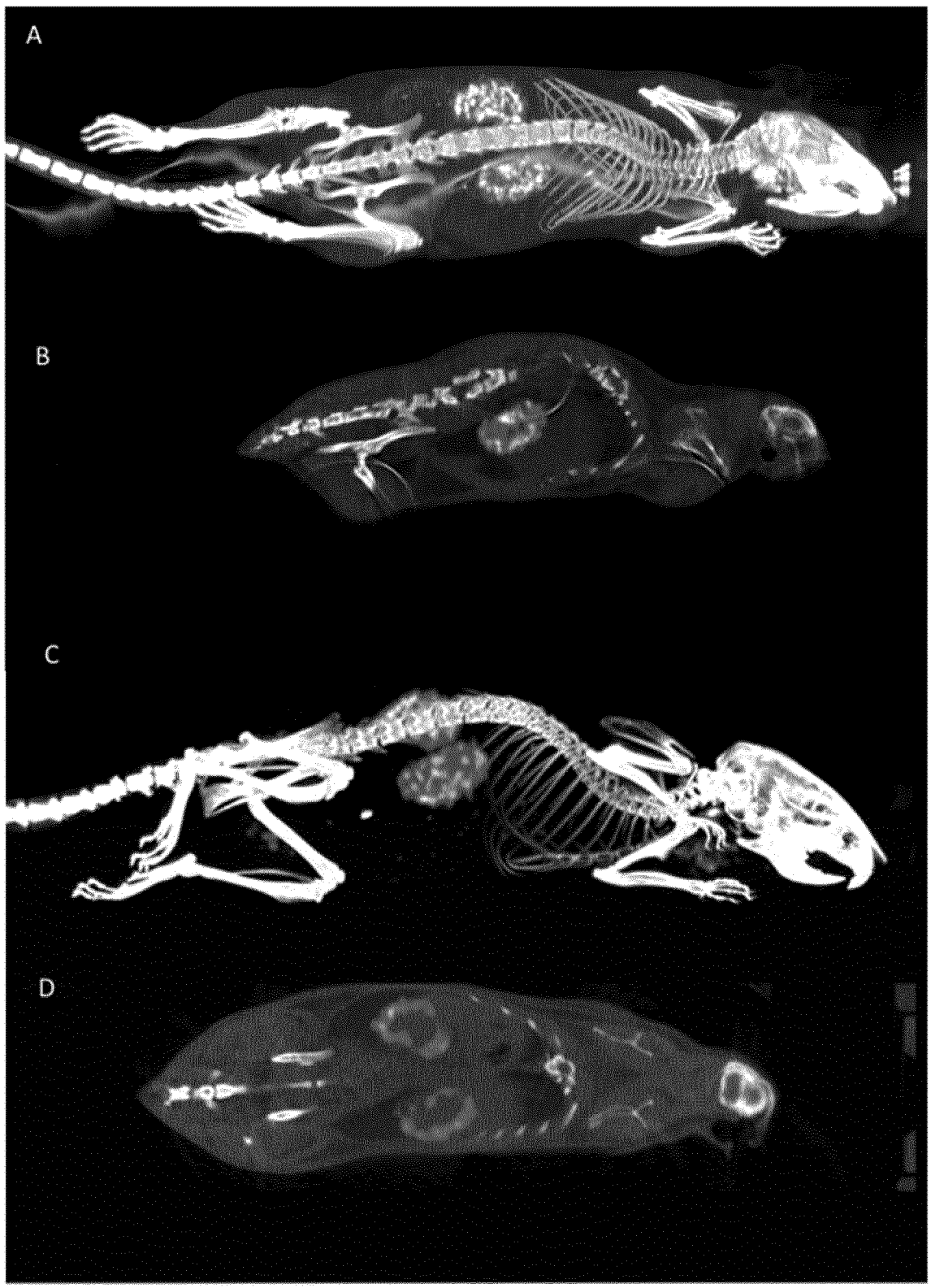

FIG. 6 show preclinical SPECT/CT images of normal NMRI mice injected with 5 MBq $^{111}$In-octreotide (A and B) and 5 MBq $^{125}$I-A1M (C and D) and imaged for 40 minutes. A and C show reconstructed three-dimensional views of the whole animal and B and D show planar section through the kidneys. Kidneys show high uptake and a concentration can be seen in the kidney cortex for both molecules. For $^{125}$I-A1M, a slight uptake in the thyroids can be observed.

Figure 7:
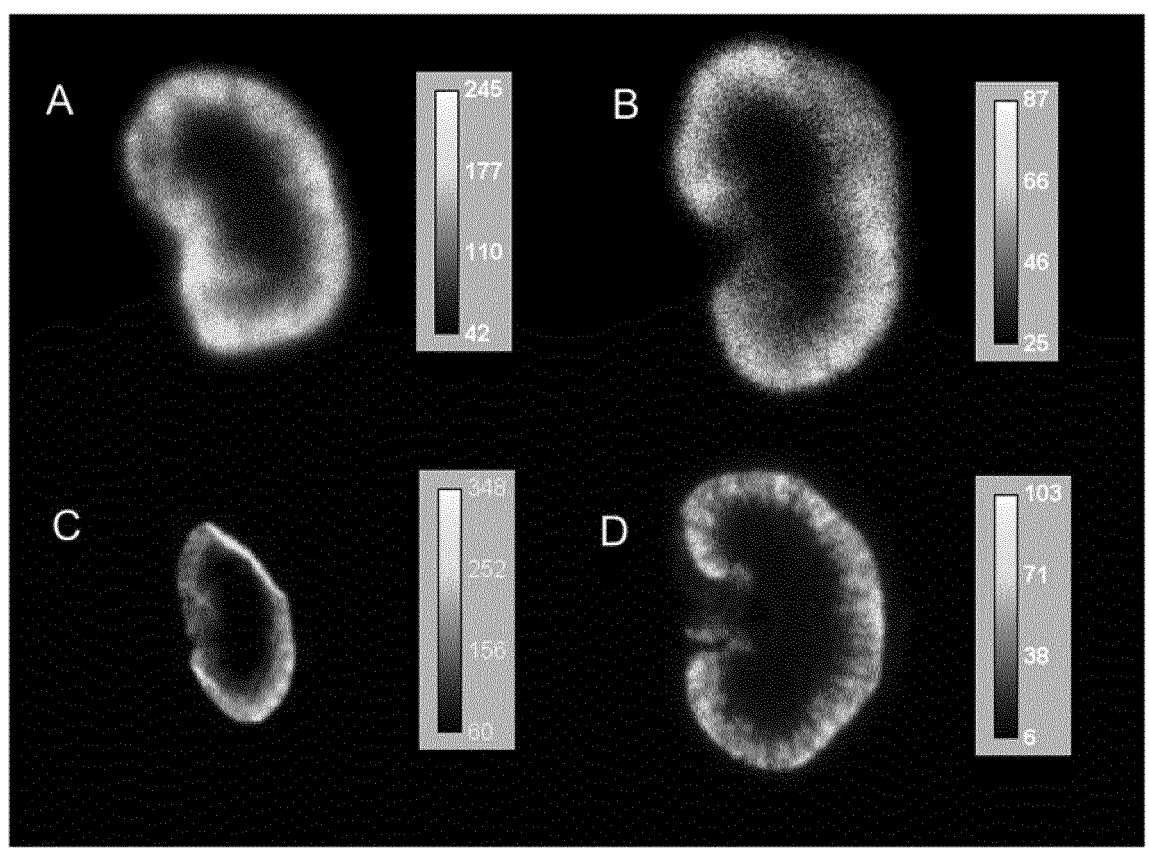

FIG. 7 show digital autoradiography images of uptake of $^{111}$In-octreotide and $^{125}$I-A1M in kidneys of normal mice. (A) $^{125}$I-A1M, 20 min p.i.; (B) $^{125}$I-A1M, 1 h p.i.; (C) $^{111}$In-octreotide, 20 min p.i.; (D) $^{111}$In-octreotide, 1 h p.i. All images shows localized uptake in the kidney cortex for both molecules. Note that the scale of each image has been adjusted to optimally illustrate the relative distribution of the radionuclides in each kidney section.

Figure 8:
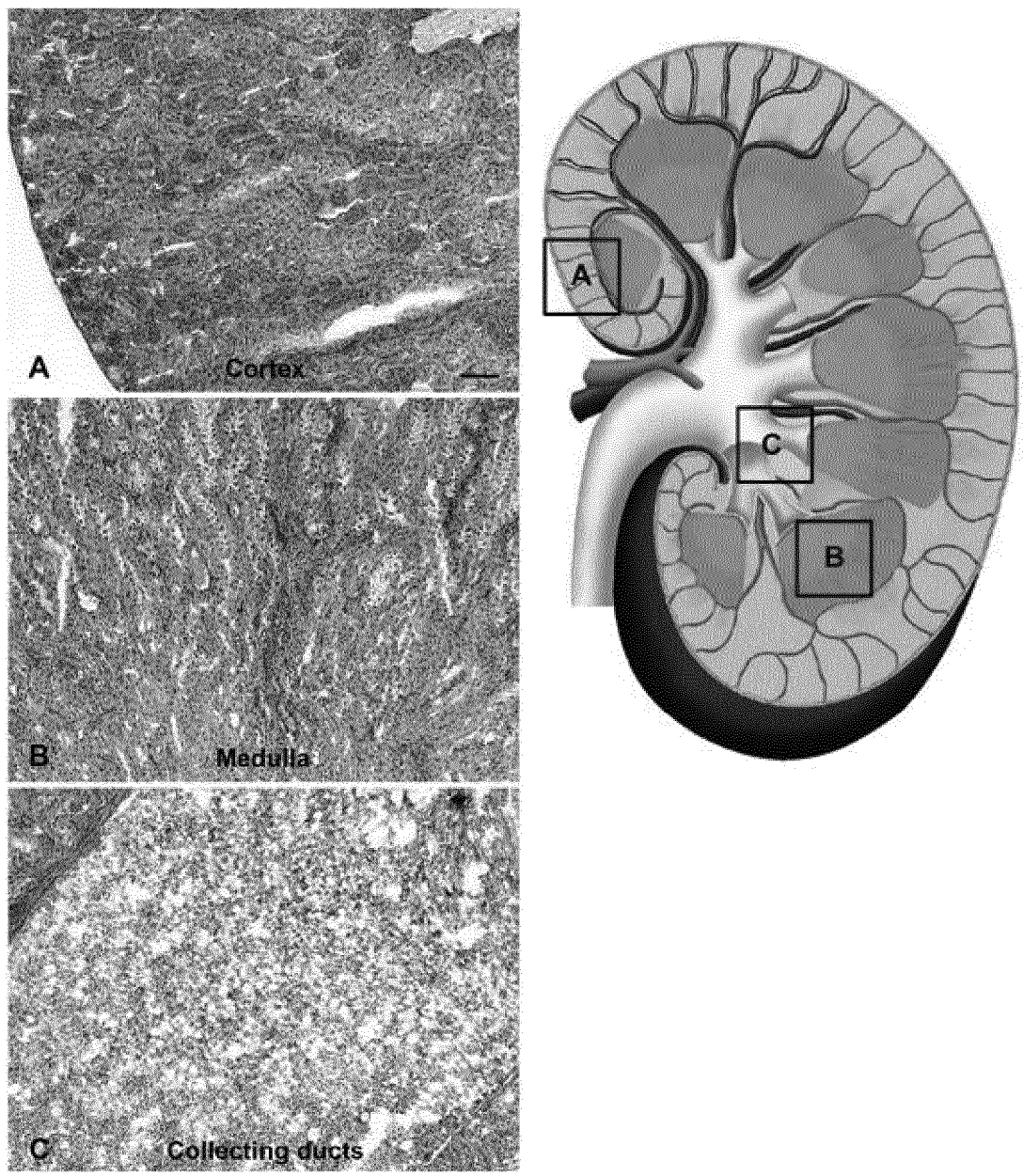

FIG. 8 shows the distribution of A1M immunoreactivity in the kidney 20 minutes after i.v. injection. A1M was injected i.v., animals were terminated after 20 minutes, and A1M immunoreactivity was detected with the K323 anti-A1M antibody, using immunohistochemistry. The left panel shows representative areas with A1M-immunoreactivity in the cortex (A), medulla (B), and collecting ducts (C); the location of these areas is indicated with A-C and highlighted with boxes in the schematic drawing in the right panel. Scale bar represents 100 µm in A-C.

Figure 9:
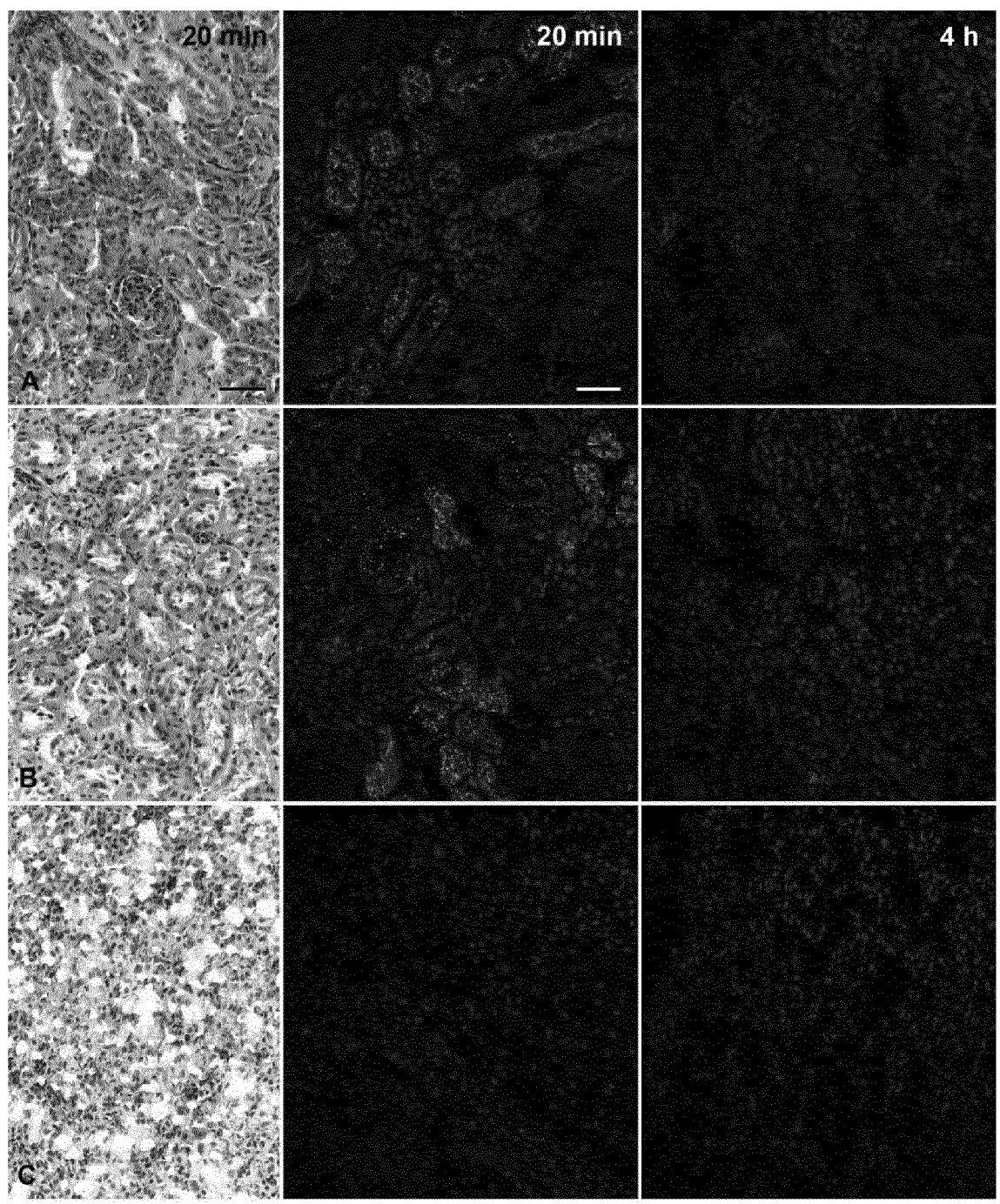

FIG. 9 shows the distribution of A1M immunoreactivity and Octreotide-A647 in the kidney 20 minutes and 4 hours after i.v. injection. A1M immunoreactivity was detected with the K323 anti-A1M antibody, using immunohistochemistry (left column; bright-field microscopy) or immunofluorescence (middle and right columns; confocal microscopy) in cortex (A), medulla (B), and collecting ducts (C). Distribution of A1M immunofluorescence (green) and Octreotide-A647 (red), and their tubular co-localization (yellow), was investigated at 20 minutes (middle) and 4 hours (right) after injection. Cell nuclei were visualized using DAPI (blue). Scale bar represents 50 µm.

Figure 10:
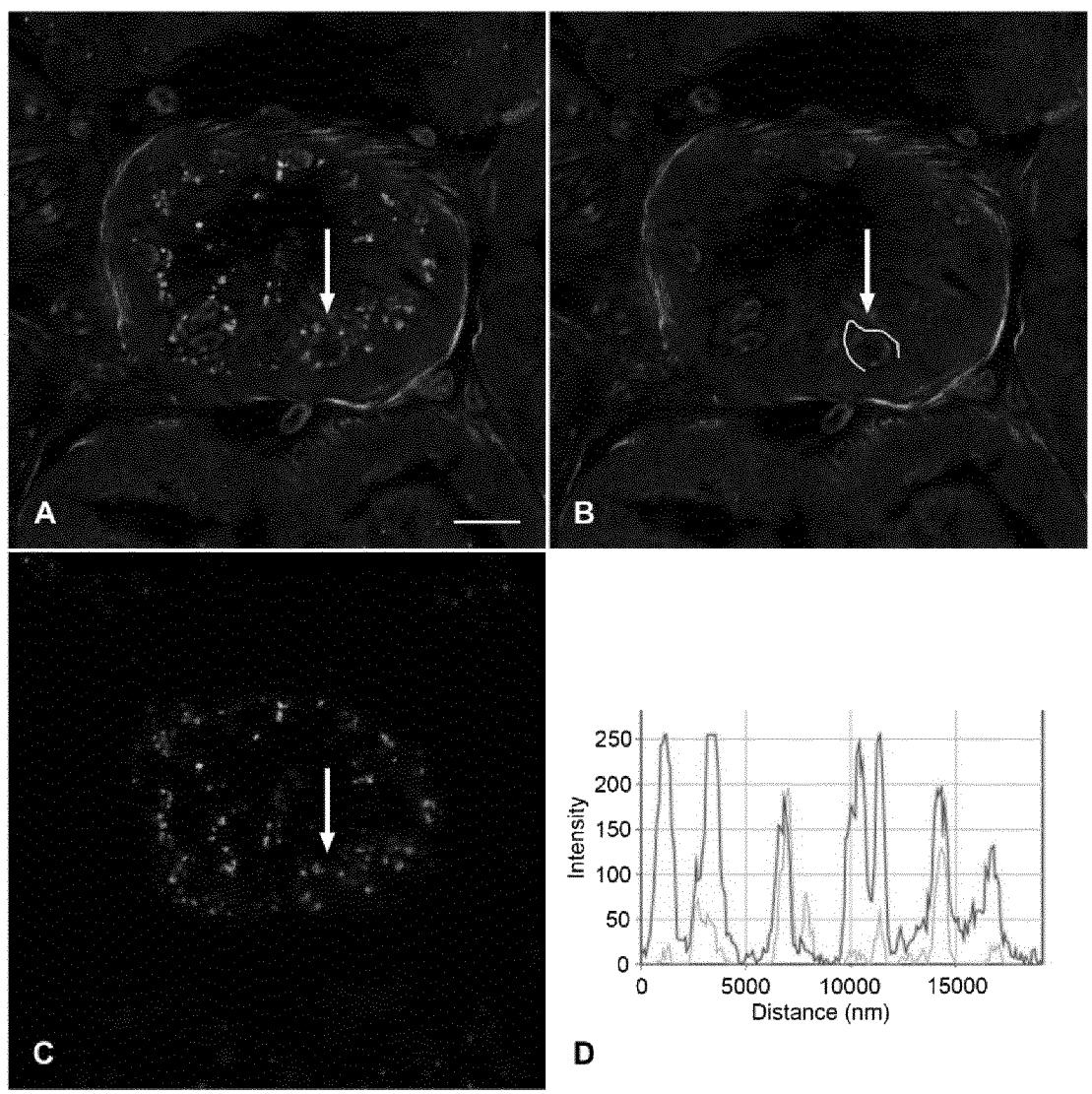

FIG. 10 shows the cellular co-localization of A1M immunofluorescence and Octreotide-A647 following i.v. injections. A1M and Octreotide-A647 conjugate were injected i.v. and animals were terminated at 20 minutes following injection. High-resolution (630.4 objective) confocal microscopic image showing the intracellular distribution of A1M immunofluorescence (green) and Octreotide-A647 fluorescence (red). Cell nuclei were stained with DAPI (blue), and phalloidin-Texas Red labeling (grey) was used to delineate tubular profiles. Resolution of punctuate fluorescence in one cell (A; arrow) was shown by measuring fluorescence intensities along a profile in the cytoplasm just outside the nucleus (B; yellow line), giving the intensities along the profile in the red and green channels (C) as an intensity profile (D) with 8 bits (256 intensity levels) per channel. Scale bar represents 10 µm.

Figure 11:
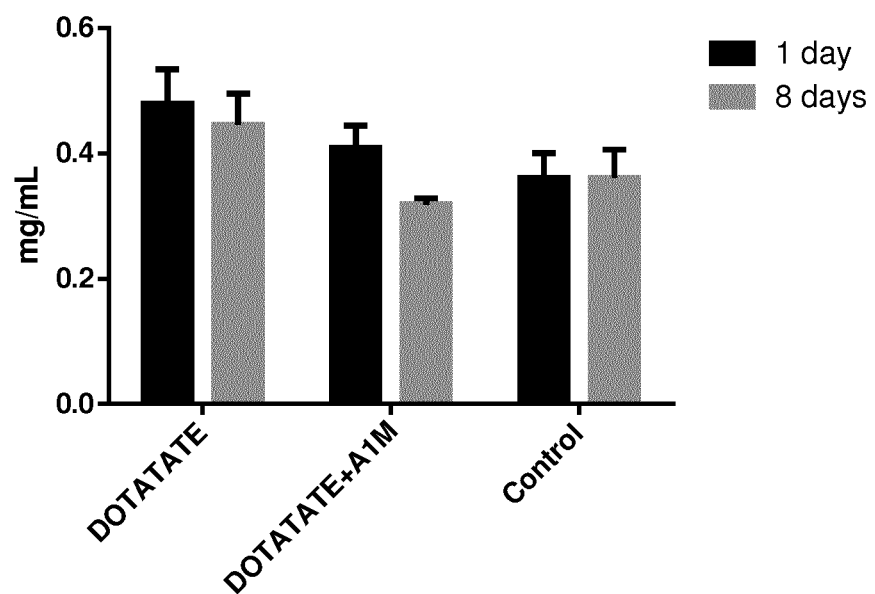
Figure 11:
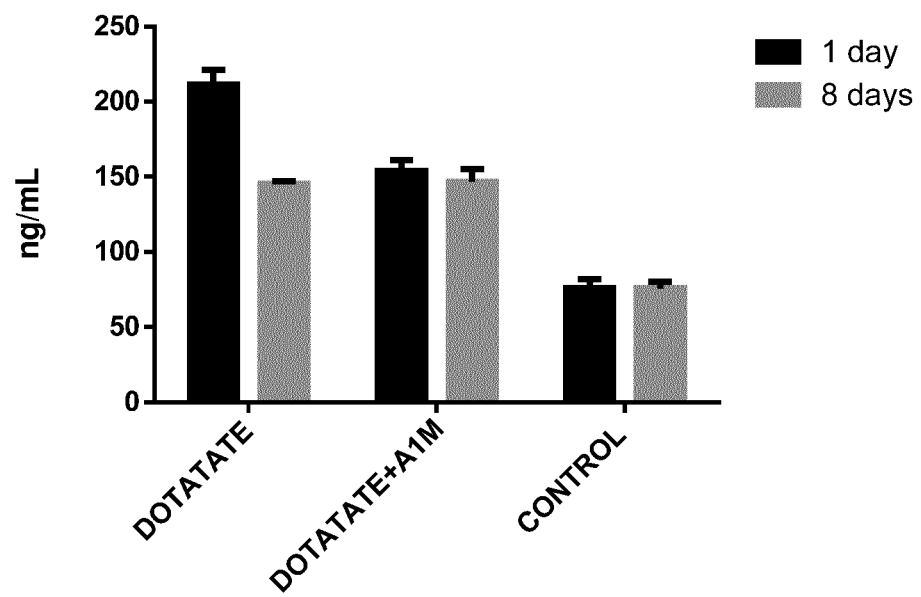

FIG. 11 shows the results of Example 2.
FIG. 12 show the sequences SEQ ID 1-4.

REFERENCES

1. John J Zaknun et al. (2013) The joint IAEA, EANM, and SNMMI practical guidance on peptide receptor radionuclide therapy (PRRNT) in neuroendocrine tumors. Eur J Nucl Med Mol Imaging, 800-16. ncbi.nlm.nih.gov/pubmed/23389427
2. Krenning E P, Bakker W H, Breeman W A, et al (1989) Localisation of endocrine-related tumors with radioiodinated analogue of somatostatin. Lancet 333, 242-244.
3. de Jong M, Krenning E P. (2002) New advances in peptide receptor radionuclide therapy. J Nucl Med 43, 617-20

4. Halliwell B, Gutteridge J M. (1994) The definition and measurement of antioxidants in biological systems. Free Rad Biol Med 16, 135-137
5. Prise K M, Folkard M, Michael B D. (2003) A review of the bystander effect and its implications for low-dose exposure. Radiat Prot Dosimetry 104(4):347-55.
6. Mothersill C, Seymour C. (2001) Radiation-induced bystander effects: past history and future directions. Radiat Res 155(6):759-67.
7. Little J B, Azzam El, de Toledo S M, Nagasawa H. (2002) Bystander effects: intercellular transmission of radiation damage signals. Radiat Prot Dosimetry 99(1-4):159-62.
8. Azzam El, de Toledo S M, Little J B. (2003) Oxidative metabolism, gap junctions and the ionizing radiation-induced bystander effect. Oncogene 22(45):7050-7.
9. Lyng F M, Seymour C B, Mothersill C. (2000) Production of a signal by irradiated cells which leads to a response in unirradiated cells characteristic of initiation of apoptosis. Br J Cancer 83(9):1223-30.
10. Lyng F M, Seymour C B, Mothersill C. (2002) Initiation of apoptosis in cells exposed to medium from the progeny of irradiated cells: a possible mechanism for bystander-induced genomic instability? Radiat Res 157(4):365-70.
11. Allhorn M, Berggård T, Nordberg J, Olsson M L, Åkerström B. (2002) Processing of the lipocalin $\alpha_1$-microglobulin by hemoglobin induces heme-binding and heme-degradation properties. Blood 99: 1894-1901.
12. Allhorn M, Klapyta A, Åkerström B. (2005) Redox properties of the lipocalin $\alpha_1$-microglobulin: reduction of cytochrome c, hemoglobin, and free iron. Free Radic Biol Med 38(5):557-67.
13. Åkerström B, Maghzal G, Winterbourn C C, Kettle A J. (2007) The lipocalin $\alpha_1$-microglobulin has radical scavenging activity. J Biol Chem 282: 31493-31503.
14. Olsson M G, Allhorn M, Bülow L, Hansson S R, Ley D, Olsson M L, Schmidtchen A, Åkerström B. (2012) Pathological conditions involving extracellular hemoglobin: Molecular mechanisms, clinical significance and novel therapeutic opportunities for $\alpha_1$-microglobulin. Antiox Redox Signal. 17(5), 813-846.
15. Åkerström B, Gram M. (2014) A1M, an extravascular tissue cleaning and housekeeping protein. Free Rad Biol Med 74C:274-282.
16. Olsson M G, Olofsson T, Tapper H, Åkerström B. (2008) The lipocalin $\alpha_1$-microglobulin protects erythroid K562 cells against oxidative damage induced by heme and reactive oxygen species. Free Rad Res. 42, 725-736.
17. May K, Rosenlöf L, Olsson M G, Centlow M, Mörgelin M, Larsson I, Cederlund M, Rutardottir S, Schneider H, Siegmund W, Åkerström B, Hansson S R. (2011) Perfusion of human placenta with haemoglobin introduces preeclampsia-like injuries that are prevented by $\alpha_1$-microglobulin. Placenta 32(4), 323-332.
18. Olsson M G, Allhorn M, Larsson J, Cederlund M, Lundqvist, K, Schmidtchen A, Sørensen O E, Mörgelin M, Åkerström B. (2011) Up-regulation of A1M/$\alpha_1$-microglobulin in skin by heme and reactive oxygen species gives protection from oxidative damage. PLoS One 6(11): e27505.
19. Olsson M G, Rosenlöf L W, Kotarsky H, Olofsson T, Leanderson T, Mörgelin M, Fellman V, Åkerström B. (2013) The radical-binding lipocalin A1M binds to a Complex I subunit and protects mitochondrial structure and function. Antiox Redox Signal. 18 (16), 2017-2028.
20. Wester-Rosenlöf L, Casslén V, Axelsson J, Edström-Hägerwall A, Gram M, Holmqvist M, Johansson M E, Larsson I, Ley D, Marsal K, Mörgelin M, Rippe B, Rutardottir S, Shohani B, Åkerström B, Hansson S R. (2014) A1M/$\alpha_1$-microglobulin protects from heme-induced placental and renal damage in a pregnant sheep model of preeclampsia. PloS One 9(1):e86353.
21. Sverrison K, Axelsson J, Rippe A, Gram M, Åkerström B, Hansson S R, Rippe B.
Extracellular fetal hemoglobin induces increases in glomerular permeability: inhibition with $\alpha_1$-microglobulin and Tempol. Am J Physiol Renal Physiol 306(4):F442-448.
22. Olsson M G, Nilsson E J C, Rutardottir S, Paczesny J, Pallon J, Åkerström B. (2010) Bystander cell death and stress response is inhibited by the radical scavenger $\alpha_1$-microglobulin in irradiated cell cultures. Rad Res 174, 590-600.
23. Rutardottir S, Nilsson E J C, Pallon J, Gram M, Åkerström B. The cysteine 34 residue of A1M/$\alpha_1$-microglobulin is essential for protection of irradiated cell cultures and reduction of carbonyl groups. Free Radic Res 47(6-7):541-550.
24. Larsson, J., Wingårdh, K., Berggård, T., Davies, J. R., Lögdberg, L., Strand, S. E. and Åkerström, B. (2001) Distribution of $^{125}$I-labelled $\alpha_1$-microglobulin in rats after intravenous injection. J. Lab. Clin. Med. 137, 165-175.
25. Kwasek A, Osmark P, Allhorn M, Lindqvist A, Åkerström B, Wasylewski Z. (2007) Production of recombinant human $\alpha_1$-microglobulin and mutated forms involved in chromophore formation. Prot Expr Purif 53, 145-152.
26. Greenwood F C, Hunter W M, Glover J S (1963) The Preparation of I-131-Labelled Human Growth Hormone of High Specific Radioactivity. Biochem J 89: 114-123.
27. Laemmli U K: Cleavage of structural proteins during the assembly of the head of bacteriophage T4, Nature 1970, 227:680-685
28. Wester L, Johansson M U, Åkerström B: Physicochemical and biochemical characterization of human $\alpha_1$-microglobulin expressed in baculovirus-infected insect cells, Protein expression and purification 1997, 11:95-103
29. Strober W, Waldmann T A: The role of the kidneys in the metabolism of plasma proteins. Nephron 1974, 13:35-66
30. Nordberg J, Allhorn M, Winqvist I, Åkerström B, Olsson M L. Quantitative and qualitative evaluation of plasma and urine $\alpha_1$-microglobulin in healthy donors and patients with different haemolytic disorders and haemochromatosis. Clin Chim Acta 2007, 386:31-37
31. Bäck T, Haraldsson B, Hulborn R, Jensen H, Johansson M E, Lindegren S, Jacobsson L. Glomerular filtration rate after alpha-radioimmunotherapy with $^{211}$At-MX35-F(ab')2: A long-term study of renal function in nude mice. Cancer Biother Radiopharm 2009, 24:649-658

Example 1

Experimental

Materials and Methods
Recombinant Human A1M
Recombinant human A1M was expressed in *E. coli*, purified and re-folded as described by Kwasek et al [25] but with an additional ion-exchange chromatography step. This was performed by applying A1M to a column of DEAE-Sephadex A-50 (GE Healthcare, Uppsala, Sweden) equilibrated with 20 mM Tris-HCl, pH8.0. A1M was eluted with a linear salt gradient (from 20 mM Tris-HCl, pH8.0 to 20 mM Tris-HCl, 0.2 M NaCl) at a flow rate of 1 ml/min. A1M-containing fractions, according to absorbance at 280 nm, were pooled and concentrated.

$^{125}$I-Labelling of A1M

Radiolabelling of A1M with $^{125}$I was done using the chloramine T method [26]. Briefly, A1M and $^{125}$I (Perkin-Elmer, NEZ033005MC) were mixed in 0.5 M sodium phosphate, pH 7.5 at final concentrations of 1 mg/ml and 10 mCi/ml, respectively. Chloramine T was added to 0.4 mg/ml and allowed to react on ice for 2 minutes, and the reaction was stopped by adding NaHSO$_3$ to 0.8 mg/ml. Protein-bound iodine was separated from free iodide by gel-chromatography on a Sephadex G-25 column (PD10, GE Healthcare, Buckinghamshire, UK). A specific activity of around 50-200 kBq/µg protein was obtained.

Octreotide

The somatostatin analogue peptide octreotide was purchased from Mallinckrodt Pharmaceuticals (mallinckrodt.com/) and labelled with $^{111}$In and with Alexa 647 (HiLyte Fluor 647; AnaSpec, Seraing, Belgium) according to instructions from the merchant. These compounds are referred to as $^{111}$In-octreotide and octreotide-647, respectively.

Animal Studies

All animal experiments were conducted in compliance with the national legislation on laboratory animals' protection and with the approval of the Ethics Committee for Animal Research (Lund University, Sweden). Male and female NMRI normal mice of 6-8 weeks old (Taconic, Ry, Denmark) were used.

Biodistribution

Biodistribution studies were conducted to determine the pharmacokinetics and biodistribution of $^{125}$I-A1M and $^{111}$In-octreotide. $^{125}$I-A1M (100 kBq, 1 µg) and $^{111}$In-octreotide (100 kBq, 10 µg) were administered i.v. through tail vein injection to NMRI mice (n=3 per injected molecule and time point). Animals were termination at 10, 20, 40, 60 minutes (both A1M and octreotide), 4 and 24 hours (octreotide) post-injection and blood and organs were sampled, weighed and measured in a NaI(TI) well counter (Wallac Wizard 1480 Wizard, Perkin Elmer). Organ-specific uptake values were calculated as percent injected activity per gram of tissue (% IA/g) or percent injected activity (% IA).

Digital Autoradiography

Digital autoradiography was performed using the Biomolex 700 imaging system (Biomolex AS, Norway). Two groups (n=2) of normal mice were i.v. injected with $^{125}$I-A1M (0.5 MBq, 5 µg) and $^{111}$In-octreotide (0.5 MBq, 50 µg). Kidneys were frozen in embedding media using dry ice and sectioned in a cryostat (Leica Microsystems AB, Sweden) in 50 µm thick sections and imaged in the Biomolex system. Images were reconstructed using in house software.

Western Blotting

SDS-PAGE analysis was performed on kidneys and serum from animals that had been injected i.v. with non-labeled A1M (100 µl/animal, 1.5 mg/ml). Animals were terminated at 10, 20 and 60 minutes post-injection, blood and kidneys were sampled and kidneys were washed and placed in 1 ml PBS. Following mechanical tissue homogenization, tissue was centrifuged at 10,000×g for 10 minutes and supernatant was transferred to a new tube and used for further analysis as describe below. Serum was obtained from the blood samples by centrifugation at 1,000×g for 10 minutes. SDS-PAGE gels were run under reducing conditions and the separated proteins were transferred to polyvinylidene difluoride (PVDF) membranes (Immobilon-P, Millipore, Bedford, Mass., USA) using Trans-Blot Turbo transfer system (Bio-Rad, Delaware, USA). PVDF membranes were subsequently blocked and incubated overnight with the IgG-fraction of rabbit polyclonal anti-A1M antiserum (K322, 5 µg/ml) as described previously [28], followed by incubation with Alexa Fluor 647 goat anti-rabbit IgG (diluted 3000×; Molecular Probes). The membranes were developed using a ChemiDoc MP Imaging system (BioRad).

SPECT Imaging

Animals were anaesthetized with 2% to 3% isoflurane gas (Baxter; Deerfield, Ill., USA) during imaging in the Nano-SPECT/CT (Bioscan, Washington D.C., USA). Animals were i.v. injected with approximately 5 MBq of $^{125}$I-A1M (approximately 30 µg) and 5 MBq of $^{111}$In-octreotide and imaged 20 m p.i. with the NSP-106 multi-pinhole mouse collimator. For $^{125}$I imaging energy windows of 20% were centered over the 35 keV photo peak and for $^{111}$In over the 175 and 241 photo peaks. SPECT data were reconstructed using HiSPECT software (SciVis; Goettingen, Germany). CT imaging was done before each whole-body SPECT. After SPECT imaging at 1 hour, kidneys were resected and embedded in Tissue-Tek® O.C.T™ compound (Sakura Finetek; Alphen aan den Rijn, The Netherlands) and frozen on dry ice. The frozen samples were cryosectioned with a thickness of 10 µm for autoradiography analysis on the Biomolex system. The kidney sections were stained with Mayer's hematoxylin and chromotrope 2R, Ch2R (both from Histolab; Gothenburg, Sweden), and scanned using a light-microscope slide scanner (Mirax Midi, Carl Zeiss; Oberkochen, Germany).

Kidney—Sample Preparation and Immunolabeling of A1M

Following simultaneous i.v. injection of 150 µg A1M (unconjugated) and 100 µg Alexa 647-labelled octreotide (octreotide-647) animals were sacrificed after 10, 20, 40, 60 minutes and 4 hours. All time-points were evaluated but only kidneys from 20 minutes and 4 hours, displaying detailed analyses at the cellular level, including laser confocal scanning microscopy and quantitative image analyses, are included. Importantly, all experiments were performed and evaluated on both wild-type and nude mice, and was shown to possess the same labeling pattern. However, only wild-type data are included.

After euthanization, kidneys were removed directly frozen and embedded in Tissue Tec. The tissue blocks were sectioned in a cryostat (Microm, HM 500OM, Walldorf, GmbH), and sections (10 µm) were collected on SuperFrost plus slides (Merck, Darmstadt, Germany). Serial sectioning was performed, collecting 3-4 sections per slide, of which adjacent slides were used for either chromogen immunohistochemistry (IHC) or immunofluorescence (IF) labeling. Sections were post-fixed in 4% paraformaldehyde (PFA, Sigma, St. Louis, Mo., USA, dissolved in PBS, 0.1 M, pH 7.4) for 15 minutes, and rinsed in PBS two times for 5 minutes.

For single labeling of A1M, sections were incubated with 0.03% hydrogen peroxide (H$_2$O$_2$, Merck, Darmstadt, Germany) for five minutes for chromogen visualization (IHC). For both chromogen and fluorescence visualization sections were incubated with 1% bovine serum albumin (BSA, Sigma, St. Louis, Mo., USA; diluted in PBS) for 30 minutes. Sections were then incubated with rabbit anti-human A1M (K:323, IgG), diluted 1:7500 (in PBS containing 1% BSA, 0.02% Triton X-100 (Sigma, St. Louis, Mo., USA) for 16 hours at 4° C.

For chromogen visualization of A1M, sections were incubated with goat anti-rabbit IgG conjugated with horseradish peroxidase (HRP, Dako Glostrup, Denmark) for 20 minutes at RT. The immunoreaction was performed via incubation in a diaminobenzidine (DAB) solution containing 0.03% H$_2$O$_2$, for 10 minutes at RT. Sections were rinsed in PBS (2×10 minutes) and counterstained with hematoxylin (Mayers, Hematoxylin Mayers Htx Histolab Products AB, Gothenburg, Sweden) followed by dehydration in a graded alcohol series and immersion in 100% Xylene. Sections were mounted and cover slipped in Pertex (Histolab Products AB, Gothenburg, Sweden).

For IF labeling of A1M, used for simultaneous detection of octreotide-647, sections were incubated with primary antibodies, as described above for chromogen detection, followed by secondary goat ant-rabbit IgG conjugated with Alexa Fluor 488 (AF488, Invitrogen, Molecular probes, USA), diluted 1:150 in PBS containing 1% BSA. Incubations were performed for 45 minutes at RT, followed by incubation in 4',6-diamidino-2-phenylindole (DAPI, nuclear labeling, Invitrogen, Molecular probes, USA) for 15 minutes at RT. A subset of sections was also incubated with phalloidin conjugated with Texas Red (binding to F-actin) for 1 hour at RT to morphologically delineate tubular structures. Sections were rinsed in PBS and were mounted and coverslipped in antifade solution (Prolong Gold, Invitrogen, Molecular probes, USA).

Optical Detection of A1M and Octreotide-647 in Kidney Sections

Chromogen single labeled A1M was visualized and digitally documented in a bright-field microscope (Leica DMRE). Digital images were collected with a Leica digital camera (DFC 500). Images used for illustrations were corrected for color balance, brightness and contrast.

For simultaneous visualization of IF-labeled A1M (A1M-AF488) and octreotide-647 at histological and cellular levels a Zeiss confocal laser scanning microscope (CLSM, LSM 510 META, Dept. Biology, Lund University) was used. Sections were inspected via scanning of emission from Alexa Fluor 488 (A1M), HiLyte Fluor 647 (octreotide), Texas Red (F-actin) and DAPI (cell nuclei).

The digital image data, one or several optical section (Z-stacks), were collected through regions of the cortex, medulla and collecting ducts. The image documentation was used for calculations of the individual presence and co-existence of A1M-AF488 and octreotide-647 fluorescence. For documentation 3 kidney areas from each section were selected as representative regions (x/y stage position marked and stored by the acquisition software ZEN 2009). Scanning (at 1024×1024 frame size) was performed with a 20×/0.8 Plan Apochromat objective (providing 1.8 µm thick optical section with about 400 nm x/y optical resolution), and with a 63×/1.4 oil immersion Plan Apochromat objective (providing 0.9 µm thick optical sections with about 250 nm x/y optical resolution). The choices of optical sections and scan depths were determined from the centre position of the majority of nuclei (DAPI labeling) in the scanned field. Sequential scanning was performed of channels displaying AF488, HiLyte Fluor 647, DAPI and Texas Red fluorescence. For each channel the renal profile with the highest fluorescence intensities was selected as a reference, from which the acquisition settings (laser power, PMT detector gain, digital offset) were optimized and used for all scanned areas. Image illustrations presented here are chosen from the individual optical sections containing areas/structures used for the quantitative measurements.

Quantitative Image Analysis of Octreotide-647 and A1M in Kidney Sections.

CLSM images of octreotide-647 fluorescence and A1M-AF488 IF were used for the quantitative analysis. The detailed distribution in renal structures (from cortex, medulla and collecting ducts) and within ductular epithelial cells was investigated. Three (3) areas per CLSM image and between 10 and 20 images per animal were analyzed. The analysis protocol was developed to use as a macro-script with ImageJ software (Version 1.49 g, Rasband, W. S. ImageJ, NIH, USA). Briefly, the CLSM images were displayed with "Stack to Images" presenting composites of all channels merged together (for AF488, HL647, DAPI and Texas Red). The selection of sample areas were made from the morphology of tubular structures and depicted by nuclear and/or phalloidin labelling. Individual regions for measurement were delimited using the lasso function.

The green (A1M-AF488) and red (octreotide-647) channels were then used as input images and the ratio of separate green or red pixels or their co-localization was investigated using the "co-localization" plug-in. Statistical analysis was performed using Origin 9.0 software (Microcal, Northampton, Mass., USA). The histogram in FIG. 5 displays representative data obtained from 3 kidneys at each time-point and are plotted as mean±SEM.

Results

Biodistribution

FIG. 1 shows in vivo biodistribution of $^{111}$In-Octreotide at 10, 20, 40 and 60 minutes post-injection and the ex vivo biodistribution of $^{125}$I-A1M at 10, 20, 40 and 60 minutes post-injection as well as 4 and 24 h post injection. Comparative uptake (% IA/g) of both molecules in the kidneys over time is illustrated as well. High uptake in the kidneys was observed for both $^{111}$In-Octreotide and $^{125}$I-A1M, with peak values at 10 and 20 minutes post-injection respectively. Size distribution of injected non-labelled A1M was investigated in blood serum and solubilized kidneys by SDS-PAGE and Western blotting. As shown in FIG. 2, A1M migrates as a homogeneous band with an apparent molecular mass around 25 kDa both in kidneys and serum at all times, and a minor, faint band around 50 kDa. The strong band most likely represents monomeric A1M with a theoretical molecular mass of 22.6 kDa and the latter the dimeric form. Highest amounts are seen at 10 minutes, supporting the kinetics of $^{125}$I-labelled A1M shown in FIG. 1, lower panel. These results show that the A1M found in blood and kidneys is intact, full-length and that the degradation therefore is negligible.

SPECT/CT Image Analysis

A qualitative SPECT/CT analysis was performed for both $^{111}$In-Octreotide and $^{125}$I-A1M and visualizes the activity distribution in the kidneys. The SPECT/CT images in FIG. 6 demonstrate a high uptake in the kidneys for both molecules. While a visibly higher concentration of $^{125}$I-A1M (FIGS. 6 C and D) in the peripheral kidney structures can be seen compared to $^{111}$In-Octreotide (FIGS. 6 A and B), both molecules seem to colocalize in the kidney cortex. A slight uptake of $^{125}$I-A1M in the thyroids can be seen as well. Activity pooled in the bladder has been omitted for $^{111}$In-Octroetide since the strong signal makes it difficult to demonstrate distribution and uptake in kidneys.

Digital Autoradiography

Digital autoradiography results displayed in FIG. 7 clearly illustrates a localization of both molecules in the kidney cortex, mirroring the SPECT/CT results. It can be observed that results are similar at 20 and 60 minutes post-injection, indicating that the localization of the peptide and protein is completed after 20 minutes. No further sub-compartmentalization can be observed in these images; however, activity distribution is not completely homogenous in the cortex. A noticeable difference in contrast and resolution can be observed between the first two images (7A and B) and the second two (7C and D). Apart from its low-energy conversion electron (30.6 keV), $^{125}$I also emits low energy x-ray photons at 27.5 and 27.2 keV. These photons contribute to the noise in the image and the proximity in energy to the conversion electrons makes them difficult to exclude from the final image.

Fluorescence Microscopy

A1M immunoreactivity was predominantly distributed in the cortex, with a decreasing immunoreactivity into the medulla and collecting ducts. Also, the intensities of A1M immunoreactive labelling was highest in the cortex, weaker in the medulla and weakest in the collecting ducts. The distribution of A1M immunoreactivity in selected areas of the kidneys 20 minutes p.i. is shown in FIGS. 8 and 9 (left panel). Strong labelling was present in a subset of tubular structures, morphologically depicted to compromise proximal tubules and subsets of glomeruli. Fluorescence double labelling of A1M and Octreotide-A647 demonstrated their tubular co-existence, as well as a high degree of cellular co-localization (FIGS. 5, 9 and 10). There was a strong labelling of both molecules, including high degree of tubular co-existence and cellular co-localization (see also FIG. 10), in the medulla and cortex 20 minutes p.i. There was a significant decrease in fluorescence detection of both molecules at 4 hours p.i., being very low in the cortex and medulla and absent in the collecting ducts (FIG. 9). A quantitative analysis of the tubular localization of both molecules was performed from CLSM images 20 minutes and 4 hours p.i., and showed a corresponding degree of co-localization 20 minutes p.i. (FIG. 5). When investigating the co-localization in tubular structures on a cellular level, as visualized and quantified in FIG. 5, similar results were seen in the cortex. The intracellular co-localization of A1M and Octreotide-A647 was demonstrated by comparisons of intensities for individual pixels in a designated profile (FIG. 5).

Example 2

Short-Term Radioprotection of Kidneys with A1M in PRRT

The materials and methods mentioned under Example 1 are also used in Example 2 unless otherwise stated below.

Purpose: Initial testing of an 8-day $^{177}$Lu-octreotide PRRT kidney damage mouse model including treatment with A1M Radionuclide activity: 150 MBq $^{177}$Lu-DOTATATE ($^{177}$Lu-DOTA0, Tyr3]octreotate)

Radiation protection and safety: 150 MBq $^{177}$Lu-DOTATATE gives 7 mSv/h at a distance of 1 cm.

A1M dose: 7 mg/kg (in vehicle 2: 10 mM Tris-HCl, pH 8.0+0.125 M NaCl)

A1M-therapy timepoint: T=0 and T=+60 min. NB, $^{177}$Lu-DOTATATE and A1M are injected separately at T=0.

Analytic Methods:

1. Blood
   | | | |
   |---|---|---|
   | Albumin & Creatinine | glomerular filtration rate | ELISA |
   | NGAL | glomerulo-tubular nephritis | ELISA |
   | Cytokines | inflammation - | Luminex - Lund |
   | KIM1 | kidney injury molecule 1 | ELISA |
   | A1M | oxidative stress | ELISA |

2. Urine
   | | | |
   |---|---|---|
   | NGAL | | ELISA |
   | Albumin & Creatinine | glomerulotubular damage | ELISA |
   | Hepcidin | | ELISA |
   | KIM1 | | ELISA |

3. Gene expression in kidneys
   | | |
   |---|---|
   | A1M | |
   | NGAL | |
   | KIM1 | |
   | Apoptosis/Necrosis | specific genes to be determined |
   | Inflammation | specific genes to be determined |
   | Microarray | |
4. Histochemistry — general tissue damage
5. Immunohistochemistry
   | | |
   |---|---|
   | Apoptosis | TUNEL, caspase |
   | Gamma H2AX | double strand breaks |
6. Autoradiography
7. Organ activity measurements Protocol:

Depending on availability (Lu-177-oct), groups will be prioritized as follows: 1 day, 8 days, 4 days.

| Group | n | Treatment | Time | Sampling | Analysis |
|---|---|---|---|---|---|
| 1 | 6 | Controls | 0 | Blood, urine | Everything |
| 2 | 4 | 177Lu-oct | Day 1 | Kidney | |
| 3 | 4 | | Day 4 | (IHC + | |
| 4 | 4 | | Day 8 | PCR) | |
| 5 | 4 | Vehicle 2 | Day 1 | Other organs | |
| 6 | 4 | | Day 4 | | |
| 7 | 4 | | Day 8 | | |
| 8 | 4 | 177Lu-oct + A1M | Day 1 | | |
| 9 | 4 | | Day 4 | | |
| 10 | 4 | | Day 8 | | |
| 11 | 4 | A1M | Day 1 | | |
| 12 | 4 | | Day 4 | | |
| 13 | 4 | | Day 8 | | |

Sample Handling:

1. Blood:
   Sample blood in tubes. Centrifuge in accordance with instructions and transfer plasma/serum to new tube. Freeze in −80° C.
2. Urine:
   Freeze in −80° C. immediately.
3. Kidneys:
   a. PCR—Dissect one kidney into 2 pieces. Place in 2 different tubes (one for mRNA and one for protein extraction) and place on dry ice.
   b. Microscopy and autoradiography
      Some kidneys imaged in Copenhagen
      Immediately dry and freeze kidney in liquid nitrogen.
4. Organ Activities:
   Use one kidney for activity analysis according to same protocol as previous studies. See also under point 6.
5. SPECT Analysis:
   Is performed on group 4 (at least 3 animals) on day 8
6. Additional Organs:
   If possible, liver, spleen, heart, intestines, gut, brain, pancreas, lung and skin is also taken care of (placed on dry ice) and activity is analyzed according to previous protocol. Organs later used for protein analysis.

Results

In the first experiment, Balb/c (nu/nu) mice were injected with either 150 MBq 177Lu-octreotide (DOTATATE), 150 MBq 177Lu-octreotide (DOTATATE)+150 µg A1M, or buffer only (control). The mice were left for 1 day or 8 days, and then sacrificed with sampling of plasma and urine, as described above. Thus, 6 groups (n=4) of samples were collected:

| | | | | |
|---|---|---|---|---|
| 1. | DOTATATE | 1 day | plasma | urine |
| 2. | DOTATATE + A1M | 1 day | plasma | urine |
| 3. | Control | 1 day | plasma | urine |
| 4. | DOTATATE | 8 days | plasma | urine |
| 5. | DOTATATE + A1M | 8 days | plasma | urine |
| 6. | Control | 8 days | plasma | urine |

As an initial estimation of kidney functions, creatinine was measured in plasma, and albumin was measured in urine samples (FIG. 11). Plasma creatinine is a marker of glomerular filtration rate (GFR), and the results suggest that DOTATATE injection resulted in significantly increased creatinine levels, i.e. decreased GFR, both after 1 and 8 days. Simultaneous infusion of A1M restored the GFR to control levels, and the effect is highly significant after 8 days ($P<0.01$). To estimate proteinuria, albumin concentrations in urine were significantly elevated by DOTATATE injections both after 1 and 8 days, and were more pronounced after 1 day. Simultaneous A1M-treatment resulted in significantly reduced proteinuria after 1 day, but not after 8 days.

To summarize, 177Lu-octreotide injections resulted in compromised kidney functions (reduced glomerular filtration and proteinuria), which could be treated with co-treatment with A1M.

SEQUENCE LISTING

```
<160> NUMBER OF SEQ ID NOS: 4

<210> SEQ ID NO 1
<211> LENGTH: 183
<212> TYPE: PRT
<213> ORGANISM: Homo sapiens

<400> SEQUENCE: 1

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Cys Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln Glu Pro
                165                 170                 175

Glu Pro Ile Leu Ile Pro Arg
            180

<210> SEQ ID NO 2
<211> LENGTH: 201
<212> TYPE: PRT
<213> ORGANISM: Homo sapiens

<400> SEQUENCE: 2

Met His His His His His His His Gly Gly Gly Gly Gly Ile Glu
1               5                   10                  15

Gly Arg Gly Pro Val Pro Thr Pro Pro Asp Asn Ile Gln Val Gln Glu
            20                  25                  30

Asn Phe Asn Ile Ser Arg Ile Tyr Gly Lys Trp Tyr Asn Leu Ala Ile
        35                  40                  45
```

Gly Ser Thr Cys Pro Trp Leu Lys Lys Ile Met Asp Arg Met Thr Val
    50                  55                  60

Ser Thr Leu Val Leu Gly Glu Gly Ala Thr Glu Ala Glu Ile Ser Met
 65                  70                  75                  80

Thr Ser Thr Arg Trp Arg Lys Gly Val Cys Glu Glu Thr Ser Gly Ala
                 85                  90                  95

Tyr Glu Lys Thr Asp Thr Asp Gly Lys Phe Leu Tyr His Lys Ser Lys
            100                 105                 110

Trp Asn Ile Thr Met Glu Ser Tyr Val Val His Thr Asn Tyr Asp Glu
        115                 120                 125

Tyr Ala Ile Phe Leu Thr Lys Lys Phe Ser Arg His His Gly Pro Thr
    130                 135                 140

Ile Thr Ala Lys Leu Tyr Gly Arg Ala Pro Gln Leu Arg Glu Thr Leu
145                 150                 155                 160

Leu Gln Asp Phe Arg Val Val Ala Gln Gly Val Gly Ile Pro Glu Asp
                165                 170                 175

Ser Ile Phe Thr Met Ala Asp Arg Gly Glu Cys Val Pro Gly Glu Gln
            180                 185                 190

Glu Pro Glu Pro Ile Leu Ile Pro Arg
        195                 200

<210> SEQ ID NO 3
<211> LENGTH: 549
<212> TYPE: DNA
<213> ORGANISM: Homo sapiens

<400> SEQUENCE: 3
ggccctgtgc caacgccgcc cgacaacatc caagtgcagg aaaacttcaa tatctctcgg      60
atctatggga gtggtacaa cctggccatc ggttccacct gcccctggct gaagaagatc     120
atggacagga tgacagtgag cacgctggtg ctgggagagg gcgctacaga ggcggagatc     180
agcatgacca gcactcgttg gcggaaaggt gtctgtgagg agacgtctgg agcttatgag     240
aaaacagata ctgatgggag gtttctctat cacaaatcca atggaacat aaccatggag     300 tcctatgtgg tccacaccac ctatgatgag tatgccattt ttctgaccaa gaaattcagc     360
cgccatcatg gacccaccat tactgccaag ctctacgggc gggcgccgca gctgagggaa     420
actctcctgc aggacttcag agtggttgcc cagggtgtgg gcatccctga ggactccatc     480
ttcaccatgg ctgaccgagg tgaatgtgtc cctggggagc aggaaccaga gcccatctta     540
atcccgaga                                                            549

<210> SEQ ID NO 4
<211> LENGTH: 603
<212> TYPE: DNA
<213> ORGANISM: Homo sapiens

<400> SEQUENCE: 4
atgcatcacc atcaccatca ccatcacggt ggaggagggg gtatcgaggg ccgcggccct      60
gtgccaacgc cgcccgacaa catccaagtg caggaaaact tcaatatctc tcggatctat     120
gggaagtggt acaacctggc catcggttcc acctgcccct ggctgaagaa gatcatggac     180
aggatgacag tgagcacgct ggtgctggga gagggcgcta cagaggcgga gatcagcatg     240
accagcactc gttggcggaa aggtgtctgt gaggagacgt ctggagctta tgagaaaaca     300
gatactgatg gaaggtttct ctatcacaaa tccaatggaa cataaccat ggagtcctat     360 gtggtccaca ccacctatga tgagtatgcc atttttctga ccaagaaatt cagccgccat     420

```
catggaccca ccattactgc caagctctac gggcgggcgc cgcagctgag ggaaactctc    480
ctgcaggact tcagagtggt tgcccagggt gtgggcatcc ctgaggactc catcttcacc    540
atggctgacc gaggtgaatg tgtccctggg gagcaggaac cagagcccat cttaatcccg    600
aga                                                                  603
```

The invention claimed is:

1. A method of treating impaired glomerular filtration rate (GFR) kidney injury in a subject in need thereof undergoing radionuclide diagnostics (RD), radionuclide therapy (RNT), or radioimmunotherapy (RIT) comprising administering a compound labelled with a radionuclide, wherein the compound labelled with a radionuclide is a somatostatin analogue selected from the group consisting of octreotide, lanreotide, Tyr$^3$-octreotide, Tyr$^3$-octreotate, DOTADOC, DODATATE, DOTA-lanreotide, pasireotide, dopastatin, and octreotide LAR, said method further comprising administering $\alpha_1$-microglobulin (A1M) to said subject, wherein the A1M has at least 95% sequence identity with SEQ ID NO: 1 or SEQ ID NO: 2.

2. The method of claim 1, wherein the A1M is administered between 60 minutes before and 30 minutes after administration of the compound labelled with a radionuclide.

3. The method of claim 1, wherein the A1M is administered between 30 minutes before and 30 minutes after administration of the compound labelled with a radionuclide.

4. The method of claim 1, wherein the A1M is administered between 10 minutes before and 10 minutes after administration of the compound labelled with a radionuclide.

5. The method of claim 1, wherein the A1M is administered simultaneously with the compound labelled with a radionuclide.

6. The method of claim 1, wherein the A1M is administered in multiple daily doses during the first week after administration of the compound labelled with a radionuclide.

7. A kit comprising a) A1M having at least 95% sequence identity with SEQ ID NO: 1 or SEQ ID NO: 2 and b) a diagnostic agent, a radionuclide therapeutic agent, or a radioimmunotherapeutic agent, said agent comprising a compound labelled with a radionuclide, wherein the compound labelled with a radionuclide is a somatostatin analogue selected from the group consisting of octreotide, lanreotide, Tyr$^3$-octreotide, Tyr$_3$-octreotate, DOTADOC, DODATATE, DOTA-lanreotide, pasireotide, dopastatin, and octreotide LAR.

8. The method according to claim 1, wherein the A1M has at least 95% sequence identity with SEQ ID NO: 1.

9. The method according to claim 1, wherein the A1M has at least 95% sequence identity with SEQ ID NO: 2.

10. The kit according to claim 7, wherein the A1M has at least 95% sequence identity with SEQ ID NO: 1.

11. The kit according to claim 7, wherein the A1M has at least 95% sequence identity with SEQ ID NO: 2.

* * * * *